United States Patent

Cossement et al.

Patent Number: 4,814,343
Date of Patent: Mar. 21, 1989

[54] SUBSTITUTED 1H-IMIDAZOLES

[75] Inventors: Eric Cossement, Brussels; Jean-Pierre Geerts, Leglise; Jean Gobert; Philippe Michel, both of Brussels, all of Belgium

[73] Assignee: U C B, S.A., Brussels, Belgium

[21] Appl. No.: 116,325

[22] Filed: Nov. 2, 1987

[51] Int. Cl.$^4$ ............... C07D 233/58; C07D 233/64; A61K 31/415
[52] U.S. Cl. .................. 514/397; 514/399; 548/336; 548/342
[58] Field of Search ........... 514/396, 399; 548/342, 548/336

[56] References Cited

U.S. PATENT DOCUMENTS

Re. 29,761 9/1978 Durant .................. 548/342

FOREIGN PATENT DOCUMENTS 0024829 3/1981 European Pat. Off.
0580047 2/1982 European Pat. Off.
0072615 2/1983 European Pat. Off.

OTHER PUBLICATIONS

Chemical Abstracts 106: 95591n (1987).

Primary Examiner—Prince E. Willis
Assistant Examiner—John F. McNally
Attorney, Agent, or Firm—Wenderoth, Lind & Ponack

[57] ABSTRACT

New substituted 1H-imidazoles and their salts, processes for the preparation thereof and pharmaceutical compositions.

These compounds have the formula

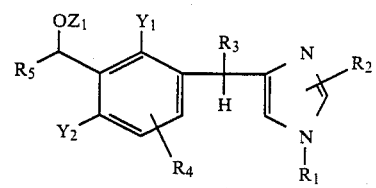

wherein
  $R_1$, $R_2$, $R_3$ and $R_5$=hydrogen or $C_1$-$C_4$-alkyl;
  $R_4$=hydrogen, $C_1$-$C_4$-alkyl or $C_1$-$C_4$-alkoxy;
  $Y_1$=hydrogen and $Y_2$=$OZ_2$ or the reverse;
  $Z_1$=$Z_2$=hydrogen or $C_1$-$C_4$-alkyl or $Z_1$ and $Z_2$=—$CH_2$— or —$C(CH_3)_2$—.

These compounds are prepared either by reducing a corresponding imidazole compound having a hydroxyl or alkoxy group on the methyl bridge between the imidazole and phenyl rings, or by hydrolyzing a 4-[[2,2-dimethyl-4H-1,3-benzodioxin-6(or 8)-yl]methyl]-1H-imidazole, or yet by reducing an alkyl 3-[(1H-imidazol-4-yl)methyl]-2-hydroxybenzoate.

These compounds have cardiac, cerebral and tissular anti-ischemic activities.

16 Claims, No Drawings

SUBSTITUTED 1H-IMIDAZOLES

The present invention relates to new substituted 1H-imidazoles and the nontoxic, pharmaceutically acceptable acid addition salts thereof, as well as to processes for the preparation thereof and the therapeutic use thereof.

It also relates to pharmaceutical compositions containing these new compounds.

European Pat. No. 24,829 describes 4-benzyl-1H-imidazoles, the benzyl group of which contains in the phenyl ring various substituents selected from hydrogen atoms and chloro, bromo, fluoro, methyl, ethyl, methoxy, amino, hydroxy and nitro groups. These compounds have anti-hypertensive, anti-ulcer, diuretic, sedative, analgesic, anti-inflammatory and tranquilizing properties.

European Pat. No. 58,047 describes similar 4-(phenylalkyl)-1H-imidazoles but in which the alkyl radical of the phenylalkyl group contains 1 to 6 carbon atoms; in most of the compounds, the imidazole ring is additionally substituted by an alkyl radical having 1 to 7 carbon atoms, a phenyl group or a substituted or unsubstituted benzyl radical. These compounds possess antithrombotic, antihypertensive, antimicrobial and antifungal properties.

European Pat. No. 72,615 describes also similar 4-benzyl-1H-imidazoles but in which the benzyl group is substituted in the alpha-position by an alkyl radical. The benzyl group contains in the phenyl ring various substituents selected from hydrogen and halogen atoms, methyl, ethyl, hydroxy and methoxy radicals and the methylenedioxy bridge between two adjacent carbon atoms. The pharmacological experiments described in this latter patent demonstrate that the compounds have antihypertensive, antithrombotic and diuretic properties. J. M. SAVOLA in Naunyn-Schmiedeberg's Arch. Pharmacol., 334, (1986), 423–9 [Chem. Abstr. 106, (1987), 95591n] has studied in rats the hypotensive and bradycardic activities of some 4-(phenylalkyl)-1H-imidazoles in which the phenyl ring is substituted on the 2-, 2,3- or 2,6-positions by methyl radicals. Amongst other effects, there is shown in that study that the introduction of a hydroxyl radical in the alpha-position of the bridge between the imidazole and phenyl rings always reduces the hypotensive and bradycardic activities.

However, an anti-ischemic activity is not mentioned in any of the aforesaid documents.

The present invention provides new, substituted 1H-imidazoles having excellent cardiac, cerebral and tissular anti-ischemic properties. These compounds may be used, inter alia, for the prevention and treatment of disorders induced by ischemias in general. Amongst these disorders, angina pectoris is a clinical expression of an acute myocardial ischemia which is the result of a momentary imbalance between the myocardial oxygen demand and the oxygen supply by the coronary circulation, which disequilibrium can lead, in every severe cases, to myocardial infarction. For this reason, the new compounds according to the present invention are especially useful for the treatment of angina pectoris and of myocardial infarction. In addition, we have also found that some of the new compounds possess a not insignificant hypotensive activity.

The new compounds according to the present invention, are substituted 1H-imidazoles having the general formula:

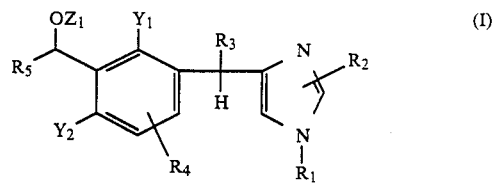

wherein $R_1$, $R_2$, $R_3$ and $R_5$, which may be the same or different, each represent a hydrogen atom or an alkyl radical having 1 to 4 carbon atoms, $R_4$ is a hydrogen atom, an alkyl radical having 1 to 4 carbon atoms or an alkoxy radical having 1 to 4 carbon atoms, one of the symbols $Y_1$ and $Y_2$ represents a hydrogen atom and the other an $OZ_2$ radical, and $Z_1$ and $Z_2$ taken separately represent both a hydrogen atom or an alkyl radical having 1 to 4 carbon atoms and $Z_1$ and $Z_2$ taken together represent a —$CH_2$— or —$C(CH_3)_2$— radical; as well as the non-toxic, pharmaceutically acceptable acid addition salts thereof.

The compounds of general formula I may be either in the form of a racemic mixture or in the form of one of the optically active (d and l) isomers when the molecule contains a single asymmetric carbon atom. When the molecule contains two asymmetric carbon atoms, the compounds are generally in the form of a mixture of diastereoisomers. These various forms are also within the scope of the present invention.

When, in general formula I, the symbols $Z_1$ and $Z_2$ each represent a hydrogen atom, a specific representative of the compounds according to the present invention is, for example, 3-[(1H-imidazol-4-yl)methyl]-2-hydroxybenzenemethanol, whereas when, in general formula I, the symbols $Z_1$ and $Z_2$ each represent an alkyl radical having 1 to 4 carbon atoms, a specific compound according to the present invention is, for example, 4-[(2,6-dimethoxy-3-methoxymethylphenyl)methyl]-1H-imidazole. In the case in which the symbols $Z_1$ and $Z_2$ taken together represent a —$CH_2$— or —$C(CH_3)_2$— radical, there may be mentioned as specific examples of compounds according to the present invention, 4-[(4H-1,3-benzodioxin-8-yl)methyl]-1H-imidazole ($Y_1=OZ_2$; $Y_2=H$), 4-[(4H-1,3-benzodioxin-6-yl)methyl]-1H-imidazole ($Y_1=H$; $Y_2=OZ_2$) and 4-[1-(2,2-dimethyl-4H-1,3-benzodioxin-8-yl)ethyl]-1H-imidazole ($Y_1=OZ_2$; $Y_2=H$).

Preferred compounds according to the present invention are the 1H-imidazoles of general formula I wherein $R_1$, $R_2$, $R_4$ and $R_5$ each represent a hydrogen atom, $R_3$ represents a hydrogen atom or an alkyl radical having 1 to 4 carbon atoms and $Z_1$ and $Z_2$ taken separately each represent a hydrogen atom and $Z_1$ and $Z_2$ taken together represent a —$CH_2$— or C-$(CH_3)_2$— radical; as well as the non-toxic, pharmaceutically acceptable acid addition salts thereof.

Compounds which are particularly preferred according to the present invention include
3-[(1H-imidazol-4-yl)methyl]-2-hydroxybenzenemethanol;
3-[(1H-imidazol-4-yl)methyl]-6-hydroxybenzenemethanol;
3-[1-(1H-imidazol-4-yl)ethyl]-2-hydroxybenzenemethanol;

3-[1-(1H-imidazol-4-yl)pentyl]-2-hydroxybenzenemethanol;

4-[(4H-1,3-benzodioxin-8-yl)methyl]-1H-imidazole and the hydrochloride thereof;

4-[1-(4H-1,3-benzodioxin-8-yl)ethyl]-1H-imidazole;

4-[(2,2-dimethyl-4H-1,3-benzodioxin-8-yl)methyl]-1H-imidazole;

4-[1-(2,2-dimethyl-4H-1,3-benzodioxin-8-yl)ethyl]-1H-imidazole; and

4-[1-(2,2-dimethyl-4H-1,3-benzodioxin-8-yl)pentyl]-1H-imidazole.

As already mentioned above, the present invention also includes the nontoxic, pharmaceutically acceptable acid addition salts of the new compounds of general formula I. Examples of pharmaceutically acceptable acids include inorganic acids, such as hydrochloric, hydrobromic, sulfuric, nitric and phosphoric acid and organic acids, such as acetic, citric, tartaric, benzoic, salicylic and maleic acid.

The substituted 1H-imidazoles of general formula I, in which $Z_1$ and $Z_2$ taken separately represent an alkyl radical having 1 to 4 carbon atoms and taken together represent a —$CH_2$— or —$C(CH_3)_2$— radical, can be prepared by reducing, according to conventional methods, an imidazole compound of the formula:

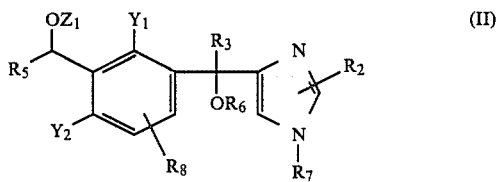

wherein $R_2$, $R_3$ and $R_5$ have the meanings given above, $R_6$ is a hydrogen atom or an alkyl radical having 1 to 4 carbon atoms, $R_7$ has the same meaning as $R_1$ given above or is a radical which can easily be removed by reduction, for example a benzyl or triphenylmethyl radical, $R_8$ has the same meaning as $R_4$ given above or is a chlorine atom, one of the symbols $Y_1$ and $Y_2$ represents a hydrogen atom and the other an $OZ_2$ radical, and $Z_1$ and $Z_2$ have the meanings given above.

This reduction is generally carried out either in glacial acetic acid or in methanol in the presence of a catalyst, for example palladium on carbon, at a temperature of from 20° to 80° C., and preferably of about 80° C., and under an atmosphere of hydrogen at a pressure of from 2 to 5 bars, or in liquid ammonia in the presence of an alkali metal, such as lithium or preferably sodium, and an auxiliary solvent, such as toluene or an ether, for example tetrahydrofuran. When a chlorine atom is present on the phenyl ring of the starting compounds of formula II ($R_8$=Cl), this chlorine atom is eliminated in the course of the reduction.

The substituted 1H-imidazoles of general formula I, in which $Z_1$ and $Z_2$ are hydrogen atoms, can be prepared by hydrolysis in an aqueous acid medium of a 4-[[2,2-dimethyl-4H-1,3-benzodioxin-6(or 8)-yl]methyl]-1H-imidazole of the formula:

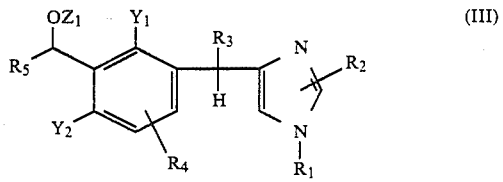

wherein $R_1$, $R_2$, $R_3$, $R_4$ and $R_5$ have the meanings given above, one of the symbols $Y_1$ and $Y_2$ represents a hydrogen atom and the other an $OZ_2$ radical, and $Z_1$ and $Z_2$ together represent the —$C(CH_3)_2$— radical.

This hydrolysis is carried out by means of a mineral acid, such as aqueous hydrochloric acid (pH 2 to 3) and at a temperature of from 20° to 100° C., for about 1 to 2 hours.

The reaction mixture is subsequently rendered alkaline to a pH of from 8 to 8.6 by means of an inorganic base, such as sodium hydroxide, and the reaction product is recovered by filtration. It is washed with water to remove the inorganic salts and then recrystallized from an appropriate solvent.

According to another embodiment, the substituted 1H-imidazoles of general formula I, in which $Y_1$=$OZ_2$ and $Y_2$, $Z_1$, $Z_2$ and $R_5$ are hydrogen atoms, can also be prepared by reduction, according to conventional methods, of an alkyl 3-[(1H-imidazol-4-yl)methyl]-2-hydroxybenzoate of the formula:

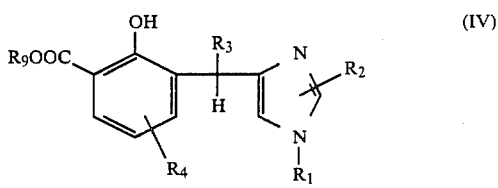

wherein $R_1$, $R_2$, $R_3$ and $R_4$, have the meanings given above and $R_9$ is an alkyl radical having 1 to 4 carbon atoms and preferably a methyl or ethyl radical.

This reduction may be carried out by means of various hydrides, preferably lithium aluminum hydride, at reflux temperature in an inert organic solvent, for example tetrahydrofuran. This latter has the advantage of giving a rapid, clean and complete reaction.

The non-toxic, pharmaceutically acceptable acid addition salts can be prepared starting from the 1H-imidazoles of formula I by per se known methods.

The starting compounds of formula II, wherein $R_6$ is a hydrogen atom and $R_7$ represents an alkyl radical having 1 to 4 carbon atoms or a radical which can easily be removed by reduction, and which are also new compounds, can be prepared by one of the two following methods:

(a) reacting an organometallic compound of formula V with a 4-($R_3$-CO)-1H-imidazole of formula VI according to the following equation:

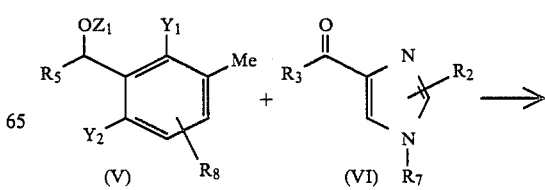

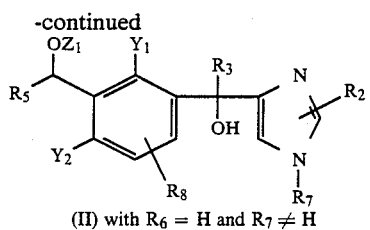

(II) with $R_6$ = H and $R_7 \neq$ H wherein $R_2$, $R_3$, $R_5$, $R_7$, $R_8$, $Y_1$, $Y_2$, $Z_1$ and $Z_2$ have the meanings given above, $R_7$ being other than a hydrogen atom and Me represents MgBr or Li;

(b) reacting a ketone of formula VII with an organomagnesium compound of formula VIII according to the following equation:

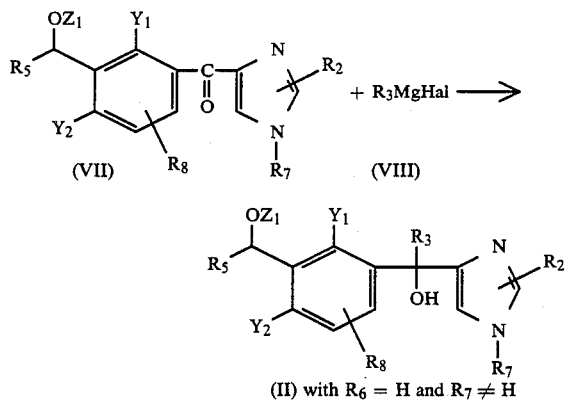

wherein $R_2$, $R_5$, $R_7$, $R_8$, $Y_1$, $Y_2$, $Z_1$ and $Z_2$ have the meanings given above, $R_3$ is an alkyl radical having 1 to 4 carbon atoms, $R_7$ being other than a hydrogen atom and Hal being a halogen atom.

The above processes (a) and (b) are preferably carried out in tetrahydrofuran under an inert atmosphere. In the case of compounds in which $Z_1$ and $Z_2$ together represent a —$CH_2$— radical, the temperature at which this exothermic reaction is carried out may reach 50° C. In the case of compounds in which $Z_1$ and $Z_2$ taken separately represent an alkyl radical having 1 to 4 carbon atoms and taken together represent a —$C(CH_3)_2$— radical, which are more sensitive to heat, the reaction temperature is generally maintained at 0° to 20° C. and, in any case, must not exceed 40° C.

The compounds of formula II prepared according to the above processes (a) and (b) and in which $R_8$ is a chlorine atom, may possibly be converted into the corresponding compounds of formula II, in which $R_8$ is a hydrogen atom, by reduction according to conventional methods.

The organometallic derivatives of formula V are obtained in known manner by the reaction of magnesium or lithium with the corresponding bromine derivatives. In the case of compounds in which $Z_1$ and $Z_2$ together represent a —$CH_2$— radical, the temperature of formation of the organometallic compound of formula V may reach 50° C. In the case of compounds in which $Z_1$ and $Z_2$ taken separately represent an alkyl radical having 1 to 4 carbon atoms and taken together represent a —$C(CH_3)_2$— radical, the temperature is kept below 40° C.

When the bromine derivatives are brominated 4H-1,3-benzodioxins ($Z_1$ and $Z_2$=—$CH_2$—), they can be prepared by reacting paraformaldehyde with an appropriate bromophenol, whereas when the derivatives are brominated 2,2-dimethyl-4H-1,3-benzodioxins ($Z_1$ and $Z_2$=—$C(CH_3)_2$—), they can be obtained by reacting 2,2-dimethoxypropane with a brominated 2-hydroxybenzenemethanol, appropriately substituted, the latter being prepared from an appropriate bromophenol and an aqueous solution of formaldehyde.

Those bromine derivatives in which $Z_1$ and $Z_2$ represent an alkyl radical having 1 to 4 carbon atoms can be prepared by alkylation of the corresponding bromophenols according to known methods.

The 4-($R_3$-CO)-1H-imidazoles of formula VI can be obtained, in a general manner, by oxidation of the corresponding 1H-imidazole-4-methanols by means of active manganese dioxide according to the method described by J. L. KELLEY, C. A. MILLER and E. W. McLEAN (J. Med. Chem., 20, (1977), 721–723).

The ketones of formula VII are prepared by oxidation of the corresponding alcohols of formula II, wherein $R_3$ and $R_6$ are hydrogen atoms, for example by the action of manganese dioxide in a chlorinated solvent, preferably in chloroform, at the boiling point, the starting alcohol of formula II being prepared by method (a) described above.

The organomagnesium compounds of formula VIII are obtained in known manner by reacting magnesium with the corresponding alkyl halide.

The starting compounds of formula II, wherein $R_6$ and $R_7$ are hydrogen atoms, are also new compounds and are prepared by reduction of a corresponding compound of formula II, in which $R_6$ is a hydrogen atom and $R_7$ is a radical which can easily be removed by reduction (for example a benzyl or triphenylmethyl radical). This reduction may be carried out in liquid ammonia in the presence of sodium. However, it is difficult to follow the course of the reaction so that it is preferable to carry out a hydrogenolysis in the presence of palladium on carbon in an alcohol, at a temperature of from 20° to 80° C. and under an atmosphere of hydrogen at a pressure of from 2 to 5 bars.

The starting compounds of formula II, wherein $R_6$ is an alkyl radical having 1 to 4 carbon atoms and $R_7$ is a hydrogen atom, are obtained by reduction in an alcohol of the formula $R_6OH$, ($R_6$ being an alkyl radical having 1 to 4 carbon atoms) of a corresponding compound of formula II, wherein $R_6$ is a hydrogen atom and $R_7$ is a radical which can easily be removed by reduction.

In most cases, this reduction does not result solely in the formation of the desired alkoxy compound of formula II ($R_6$=alkyl; $R_7$=H), but a mixture of this alkoxy compound and of the corresponding alcohol of formula II ($R_6$=$R_7$=H) is obtained. This mixture is generally used as such for carrying out the following step of eliminating the $OR_6$ radical by reduction. However, if desired, the alcohol of formula II ($R_6$=$R_7$=H) and the alkoxy compound of formula II ($R_6$=alkyl; $R_7$=H) may be isolated in a pure state, for example by chromatography of the mixture.

Furthermore, the hydrochlorides of the alcohols of formula II $R_6$=$R_7$=H) can easily be converted into the hydrochlorides of the alkoxy compounds of formula II ($R_6$=alkyl; $r_7$=H) by simply heating in the corresponding alcohol of formula $R_6OH$.

When a chlorine atom is present on the phenyl ring of the starting compound of formula II ($R_8$=Cl), it is generally eliminated at the same time as the easily removable R7 radical in the course of the reduction processes described hereinbefore.

The 4-[[2,2-dimethyl-4H-1,3-benzodioxin-6(or 8)-yl]methyl]-1H-imidazoles of formula III are prepared by reduction, according to conventional methods, of a compound of formula II, wherein $R_2$, $R_3$, $R_5$, $R_6$, $R_7$, $R_8$, $Y_1$ and $Y_2$ have the meanings given above and $Z_1$ and $Z_2$ together represent the —C(CH$_3$)$_2$— radical.

This reduction is generally carried out either in glacial acetic acid or in methanol in the presence of a catalyst, for example palladium on carbon, at a temperature of from 20° to 80° C. and preferably of about 80° C. under an atmosphere of hydrogen at a pressure of from 2 to 5 bars or in liquid ammonia in the presence of an alkali metal, such as lithium or preferably sodium, and in an auxiliary solvent, such as toluene or an ether, for example tetrahydrofuran. A chlorine atom possibly present on the phenyl ring of the starting compound of formula II ($R_8$=Cl) is eliminated in the course of this reduction.

The alkyl 3-[(1H-imidazol-4-yl)methyl]-2-hydroxybenzoates of formula IV used as starting materials may be prepared by a multi-step process:

(a) reacting in the presence of sodium ethoxide an alkyl 2-oxocyclohexanecarboxylate of formula IX with a 4-chloromethyl-1H-imidazole of formula X to give an alkyl 1-[(1H-imidazol-4-yl)methyl]-2-oxocyclohexanecarboxylate of formula XI according to the equation:

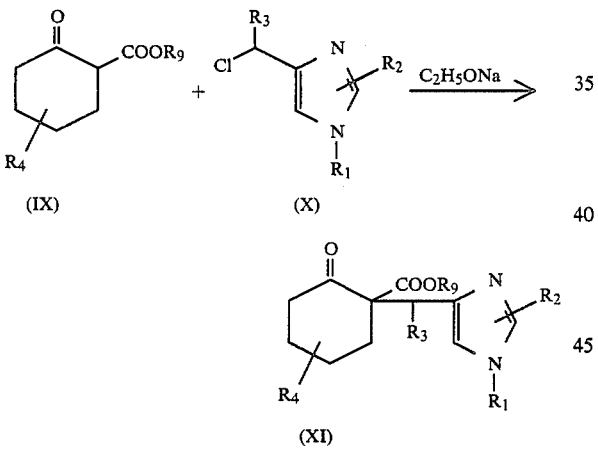

(b) heating the alkyl 1-[(1H-imidazol-4-yl)methyl]-2-oxo-cyclohexanecarboxylate of formula XI for several hours at a temperature of about 100° to 105° C. in the presence of an excess of sodium ethoxide, which results in the rearrangement of the molecule to give an alkyl 3-[(1H-imidazol-4-yl)methyl]-2-oxocyclohexanecarboxylate of formula XII according to the equation:

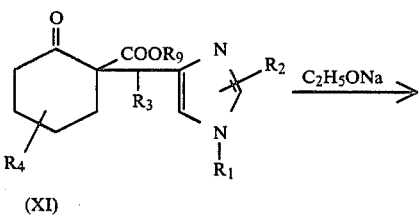

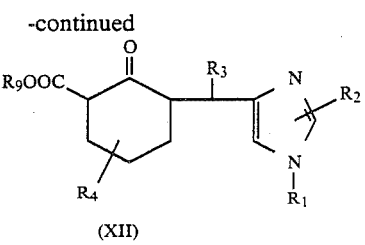

(c) oxidizing the alkyl 3-[(1H-imidazol-4-yl)methyl]-2-oxo-cyclohexanecarboxylate of formula XII with bromine in acetic acid at reflux temperature for several hours to give a mixture of alkyl 3-[(1H-imidazol-4-yl)methyl]-2-hydroxybenzoate and of its derivatives brominated in the 2- and/or 5-position of the imidazole ring, then hydrogenolyzing the resulting mixture in the presence of palladium on carbon and of rhodium on carbon under a hydrogen pressure of 3.5 bars, which finally gives the alkyl 3-[(1H-imidazol-4-yl)methyl]-2-hydroxybenzoate of formula IV according to the equation:

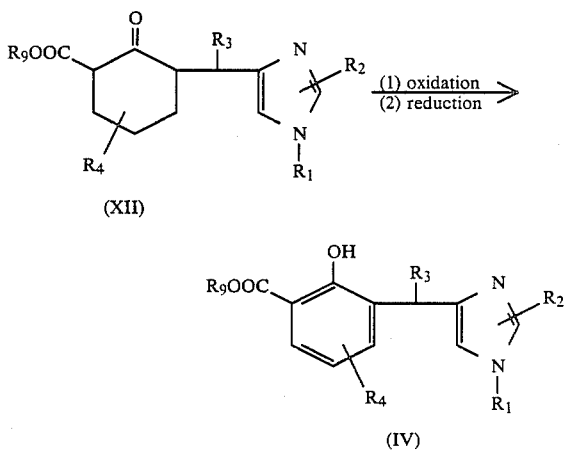

In the above formulae, $R_1$, $R_2$, $R_3$ and $R_4$ have the meanings given above and $R_9$ is an alkyl radical having 1 to 4 carbon atoms and preferably a methyl or ethyl radical.

The 4-chloromethyl-1H-imidazoles of formula X can be prepared from the corresponding 1H-imidazole-4-methanols by chlorination according to known methods.

As already mentioned above, the new substituted 1H-imidazoles of formula I, as well as their non-toxic, pharmaceutically acceptable acid addition salts, possess excellent cardiac, cerebral and tissular anti-ischemic properties. The pharmacological tests described hereinafter provide evidence of these important properties.

The following compounds according to the present invention have been subjected to the pharmacological tests:

3-[(1H-imidazol-4-yl)methyl]-2-hydroxybenzenemethanol (compound A);

3-[(1H-imidazol-4-yl)methyl]-2-hydroxy-5-methyl-benzenemethanol (compound B);

3-[(1H-imidazol-4-yl)methyl]-6-hydroxybenzenemethanol (compound C);

4-[(6-methyl-4H-1,3-benzodioxin-8-yl)methyl]-1H-imidazole hydrochloride (compound D);

4-[(4H-1,3-benzodioxin-8-yl)methyl]-1H-imidazole hydrochloride (compound E);
4-[(2,2-dimethyl-4H-1,3-benzodioxin-8-yl)methyl]-1H-imidazole (compound F);
4-[(2,2,6-trimethyl-4H-1,3-benzodioxin-8-yl)methyl]-1H-imidazole (compound G);
4-[1-(4H-1,3-benzodioxin-8-yl)ethyl]-1H-imidazole (compound H);
4-[1-(2,2-dimethyl-4H-1,3-benzodioxin-8-yl)pentyl]-1H-imidazole (compound I);
3-[1-(1H-imidazol-4-yl)pentyl]-2-hydroxybenzenemethanol (compound J);
4-[[2,6-dimethoxy-3-(1-methoxyethyl)phenyl]methyl]-1H-imidazole hydrochloride (compound K);
4-[1-(2,2-dimetyl-4H-1,3-benzodioxin-8-yl)ethyl]-1H-imidazole (compound L);
3-[1-(1H-imidazol-4-yl)ethyl]-2-hydroxybenzenemethanol (compound M);
d-4-[1-(4H-1,3-benzodioxin-8-yl)ethyl]-1H-imidazole (compound N).

1. Cardiac anti-ischemic activity 1.1 In rats

In an anesthetized and thoracotomized rat, a coronary ligature induces a stable cardiac ischemia (see H. SELYE et al., Angiology, 11, (1960), 398–407) which results in an elevation of the R wave of the epicardial electrocardiogram (see L. G. T. RIBEIRO et al., J. Electrocardiol., 12, (1979), 89–95). The anti-ischemic action of a compound results in a reduction of the elevation of the R wave.

Table I shows, for the compounds subjected to the test, the dose ($DE_{20}$ in mg/kg) which, administered intravenously to a group of 5 rats, produces an average reduction of at least 20% of the elevation of the R wave on the group of animals. The following compounds were used as reference compounds:

propanolol: 1-(isopropylamino)-3-(1-naphthyloxy)-2-propanol;
verapamil: alpha-[3-[[2-(3,4-dimethoxyphenyl)ethyl]methylamino]propyl-3,4-dimethoxy-alpha-(1-methylethyl)benzeneacetonitrile;
nifedipine: dimethyl 1,4-dihydro-2,6-dimethyl-4-(2-nitrophenyl)-3,5-pyridinecarboxylate.

TABLE I

| Test compound | $DE_{20}$ (in mg/kg) |
| --- | --- |
| A | 0.006 |
| B | 0.22 |
| C | 0.20 |
| D | 0.09 |
| E | 0.25 |
| F | 0.24 |
| G | 0.26 |
| J | 0.26 |
| L | 0.03 |
| M | 0.02 |
| N | <0.23 |
| propanolol | 9.47 |
| verapamil | 0.32 |
| nifedipine | 1.70 |

1.2. In dogs

In the awake dog bearing a coronary pneumatic occluder, the coronary occlusion induces an elevation of the S-T segment of the epicardial electrocardiogram. The anti-ischemic action of a compound results in a reduction of the elevation of the S-T segment (see P. R. MAROKO and E. BRAUNWALD, Circ., 53, (1976, Suppl.I), 162–168; S. E. EPSTEIN et al., Circ. 53, (1976, Suppl.I), 191–197).

Table II shows, for the compounds subjected to the test, the dose ($DE_{20}$ in mg/kg) which, administered intravenously to a group of 10 animals, produces an average reduction of at least 20% of the elevation of the S-T segment on the group of animals.

TABLE II

| Test compound | $DE_{20}$ (in mg/kg) |
| --- | --- |
| A | 0.002 |
| B | 0.02 |
| C | 0.02 |
| D | 0.09 |
| E | 0.01 |
| F | 0.24 |
| G | 0.26 |
| H | 0.007 |
| I | 0.1 |
| J | 0.03 |
| K | 0.31 |
| L | 0.008 |
| M | 0.0007 |
| propanolol | 0.53 |

From these Tables, it can be seen that the compounds according to the present invention are very active and superior to the reference compounds.

2. Cerebral anti-ischemic activity

Ligature of the two carotids in anesthetized mice progressively induces the death of at least half of the animals after 90 minutes.

In this test, to a group of 18 animals, there is administered intraperitoneally, 30 minutes before making the ligatures, a dose of 0.2 mg/kg of compound A dissolved in 10 ml of physiological salt solution. A control group, also composed of 18 animals, only received at the same moment the physiological salt solution (a 0.9% aqueous solution of sodium chloride). There is subsequently noted, 30 and 90 minutes after making the ligatures, the number of surviving animals in the control group and in the treated group. The results obtained are given in Table III:

TABLE III

| Test compound | Number of surviving animals | | Duration (min) |
| --- | --- | --- | --- |
| | Control group | Treated group | |
| A | 12/18 | 17/18 | 30 |
| A | 9/18 | 15/18 | 90 |

This Table shows that compound A significantly increases the number of surviving animals in the group treated with compound A in comparison with the number of surviving animals in the control group. The protection achieved and calculated according to ABBOTT'S formula (see FINNEY, Statist. Meth. in Biol. Assay, 2nd edn., 1964) is 66% after 90 minutes.

3. Tissular anti-ischemic activity

In animal physiopathology, the accumulation of calcium ions in ischemic tissue is an indication of the state of suffering of the cells (see A. D. SHARMA et al., J. Clin. Invest., 72, (1983), 802–818). A coronary artery occlusion of long duration (150 minutes) carried out on anesthetized rats results in an accumulation of calcium ions (+250%) in the tissue of the necrotized region.

In this test, the compound tested is administered intravenously over a period of 1 minute, 10 minutes before coronary artery occlusion, to a group of at least 6 rats, at a dose of 100 μg/kg dissolved in 0.8 ml physiological salt solution. This administration is immediately followed by a slow infusion of the test compound at a dose of 100 μg/kg/hour for 2.5 hours. The necrotized zone is dissected out and tissue calcium ion accumulation is measured by atomic absorption spectrometry according to the procedure described by Hideto OHHARA et al. (J. Mol. Cell. Cardiol., 14, (1982), 13-20). A control group composed of at least 6 rats only received the physiological salt solution.

The activity of compound A is compared with verapamil administered under the same conditions; however there is used a dose of 320 μg/kg of verapamil instead of 100 μg/kg.

In the following Table IV, there is given the decrase (in %) of the mean calcium ion concentration in the ischemic tissue of the treated group in comparison with the mean calcium ion concentration in the ischemic tissue of the control group. The results show that although the dose administered is 3 times lower than that of verapamil, compound A ismore than twice as active for combating the infiltration of calcium into the tissue of the necrotized region.

TABLE IV

| Test compound | Decrease of the calcium ion concentration in the tissue (in %) |
|---|---|
| verapamil | 18 |
| A | 40 |

4. Toxicity

The toxicity of the compounds according to the present invention has been determined in male NMRI mice by means of Irwin's test (S. IRWIN, Psychopharmacologia, 13, (1968), 222-257).

Progressive doses of the test compound are administered intraperitoneally to groups of three mice until the lethal dose is reached (dose bringing about the death of 2 out of 3 animals within 48 hours).

The following Table V gives the lethal dose in mg/kg found for the compounds according to the present invention. It can be seen from this Table that the compounds according to the present invention are not very toxic, the lethal dose being well above the active doses.

TABLE V

| Test compound | Lethal dose (in mg/kg) |
|---|---|
| A | 204 |
| B | >218 |
| C | 613 |
| D | 80 |
| E | 253 |
| F | 73 |
| G | 258 |
| H | 69 |
| I | 300 |
| J | 260 |
| K | 31.2 |
| L | 25.8 |

The pharmaceutical compositions containing the compounds according to the present invention may be administered orally, parenterally or rectally.

The pharmaceutical compositions which can be used for oral administration may be solid or liquid, for example in the form of coated or uncoated tablets, pills, dragees, gelatine capsules, solutions, syrups and the like. The compositions which can be used for parenteral administration are the pharmaceutical compositions known for this mode of administration, for example aqueous or oily solutions, suspensions or emulsions. For rectal administration, the compositions containing the compounds of the present invention are generally used in the form of suppositories.

The pharmaceutical forms, such as injectable solutions, injectable suspensions, tablets, drops, suppositories and the like, are prepared by the methods currently used by pharmacists. The compounds of the present invention are mixed with a solid or liquid, non-toxic and pharmaceutically acceptable carrier and optionally with a dispersing agent, a disintegration agent, a stabilizing agent and the like. If desired, sweetening and coloring agents and the like may also be added.

The percentage of active compound in the pharmaceutical compositions may be varied within wide limits, according to the patient and the mode of administration and especially according to the frequency of administration.

With regard to the daily posology, it may be varied within a wide range of dosage units, for example from 0.1 μg to 1 mg of active compound, depending upon the mode of administration. Thus, for example, the daily dosage may be from 0.1 μg to 160 μg, preferably from 1 μg to 80 μg, when the compound is administered intravenously.

As a non-limiting Example of a composition containing a compound of the present invention, the following formulation of a sterile solution for intravenous administration is given:

| compound A | 250 μg |
|---|---|
| sodium acetate | 19.15 mg |
| sodium chloride | 81 mg |
| acetic acid | 3.59 mg |
| sterile water ad | 10 ml |

The following Examples are given for the purpose of illustrating the preparation of the 1H-imidazoles according to the present invention, as well as of their intermediates. In these Examples, the nuclear magnetic resonance (NMR) spectra were determined with a Perkin-Elmer apparatus at 60 MHz, using tetramethylsilane as internal reference; the chemical shifts are indicated in delta (ppm). The letters s, d, t, q, m and J indicate, respectively, a singlet, doublet, triplet, quartet, multiplet and the coupling constants in Hertz.

EXAMPLE 1

Preparation of starting compounds of formula II ($R_6$=H; $R_7$=$C_1$-$C_4$-alkyl or triphenylmethyl) by method (a)

A.

Preparation of the bromine derivatives precursors of the organometallic derivatives of formula V

1

8-Bromo-6-chloro-4H-1,3-benzodioxin 1.a

2-Bromo-4-chlorophenol

This compound is prepared according to the method of I. I. LAPKIN et al. (see Zh. Obshch. Khim., 35, (2) (1965), 251-253; Chem. Abstr. 62, (1965), 13111).

1.b

8-Bromo-6-chloro-4H-1,3-benzodioxin

Into a mixture of 229 ml of concentrated sulfuric acid and 620 ml of acetic acid, cooled to 15° C. there is added all at once 311 g of paraformaldehyde (previously washed with 200 ml of acetic acid), followed by 462.6 g (2.23 moles) of 2-bromo-4-chlorophenol. The reaction mixture is stirred for 148 hours at 15° C. It is then neutralized with 3.1 liters of a 7.8N aqueous solution of sodium hydroxide. The precipitate formed is filtered off, dried and then dissolved in toluene. The solution is dried over anhydrous sodium sulfate and then distilled. The residue is stirred in hexane and allowed to crystallize. 364 g of 8-bromo-6-chloro-4H-1,3-benzodioxin are obtained. Yield: 65.5% of theory; M.P.: 108°–110° C.

| Analysis for $C_8H_6BrClO_2$ in %: | | | | |
|---|---|---|---|---|
| calc.: | C | 38.47 | H | 2.40 |
| found: | | 38.9 | | 2.51 |

2

6-Bromo-4H-1,3-benzodioxin

This compound is pdrepared as described in 1.b. hereinabove, starting from the following quantities of reactants: 3.8 liters of acetic acid, 654 ml of concentrated sulfuric acid, 1 kg (5.78 moles) of 4-bromophenol and 870 g (28.9 moles) of paraformaldehyde. The duration of the reaction is 120 hours at 0° C.

After neutralization of the reaction mixture with a solution containing 1350 g of sodium hydroxide dissolved in 13 liters of water, the precipitate obtained is filtered off and then dissolved in 7 liters of toluene. The organic phase is dried by azeotropic distillation, filtered hot to remove formaldehyde polymers and then evaporated under reduced pressure. The residue is distilled under reduced pressure. 933 g of 6-bromo-4H-1,3-benzodioxin are obtained. Yield: 75% of theory; B.P.: 80°–90° C./0.13 mbar. The product crystallizes when stirred in a mixture of diisopropyl ether/hexane; M.P.: 43°–47° C.

NMR (CDCl$_3$): delta 4.88 (2H, s, Ar—CH$_2$), 5.24 (2H, s, —OCH$_2$O—), 6.39 (1H, d, J=8.7 Hz, ArH), 7.13 (1H, m, ArH), 7.31 (1H, dd, J=8.7 and 2.4 Hz, ArH).

3

8-Bromo-6-chloro-2,2-dimethyl-4H-1,3-benzodioxin

3.a

3-Bromo-5-chloro-2-hydroxybenzenemethanol 880 g (4.241 moles) of 2-bromo-4-chlorophenol are dissolved in 8.2 liters of a 38% aqueous solution of formaldehyde (about 100 moles). The mixture is cooled on an ice-bath, and then mixed with 1380 g (24 moles) of potassium hydroxide added in 100 g portions. The addition is carried out over a period of 150 minutes at a temperature of from 18° to 23° C. Stirring is continued for 2 hours at ambient temperature and then the reaction mixture is heated progressively on a water-bath to 40° C. The reaction is slightly exothermic and the temperature of the mixture stabilizes at about 45° C. Stirring is then continued for 178 hours at 40° C.

The reaction mixture is subsequently cooled. 2 liters of water are added followed by acidification to pH 3 by means of 1420 ml of concentrated hydrochloric acid. Extraction is caried out with 2 liters of dichloromethane and then 6 times with 1 liter of dichloromethane. The organic phase is washed with 2 liters of water, dried over anhydrous sodium sulfate and the solvent evaporated under reduced pressure.

The crude residue obtained (1490 g) contains about 68.8% of 3-bromo-5-chloro-2-hydroxybenzenemethanol and aboout 23.8% of 2-bromo-4-chlorophenol starting material which has not reacted. This mixture is used as such in the following step.

3.b

8-Bromo-6-chloro-2,2-dimethyl-4H-1,3-benzodioxin

The 1490 g of crude residue obtained in the precedfing step are dissolved in 20 liters of toluene and 4.68 liters of 2,2-dimethoxypropane in the presence of 296 g of montmoriloonite K10 (freshly dehydrated by azeotropic distillation with toluene). The temperature of the mixture increases to 30° C.; stirring is maintained at this temperature for 115 hours. The reaction mixture is filtered and the toluene is eliminated under reduced pressure. The residue obtained is purified by distillation under reduced pressure. 527 g of 8-bromo-6-chloro-2,2-dimethyl-4H-1,3-benzodioxin are obtained with a purity of 90% (analysis by HPLC chromatography); B.P.: 100°–112° C./0.026 mbar. Total yield: 75% of theory (based on the amount of 2-bromo-4-chlorophenol used).

NMR (CDCl$_3$): delta 1.55 (6H, s, C(CH$_3$)$_2$), 4.78 (2H, s, CH$_2$), 6.9 (1H, m, ArH), 7.4 (1H, m, ArH).

4

6-Bromo-2,2-dimethyl-4H-1,3-benzodioxin

4.a

5-Bromo-2-hydroxybenzenemethanol

This compound is prepared as described in 3.a. hereinabove, starting from 4-bromophenol. After evaporation of the dichloromethane used for the extraction, there are obtained 709 g of residue which is chromatographed on 1.2 kg of silica (eluent:dichloromethane). After evaporation of the solvent, there are obtained 602 g of residue containing about 50% of the desired 5-bromo-2-hydroxybenzenemethanol (analysis by HPLC chromatography). This residue is used as such in the next step.

4.b

6-Bromo-2,2-dimethyl-4H-1,3-benzodioxin 572 g of the residue obtained in the preceding step are dissolved in 12.5 liters of dry toluene and 2.94 liters of 2.2-dimethoxypropane. 186 g of montmorillonite K10 are added thereto and the mixture is stirred for 25 hours at ambient temperature. It is then filtered, the organic phase is distilled under reduced pressure and the residue is redissolved in 600 ml of toluene. This solution is passed through a column containing 3 kg of alumina (eluent: 6 liters of toluene). The eluate is evaporated under reduced pressure and gives 180 g of residue is distilled under reduced pressure. 60 g of 6-bromo-2,2-dimethyl-4H-1,3-benzodioxin are obtained. B.P.: 110°–130° C./0.027 mbar. The yield, based on the amount of 4-bromophenol used as starting material, is about 10%.

NMR (CDCl$_3$): delta 1.52 (6H, s, C(CH$_3$)$_2$), 4.80 (2H, s, CH$_2$), 6.71 (1H, d, J=7.9 Hz, ArH), 7.07–7.5 (2H, m, ArH).

5

8-Bromo-2,2,6-trimethyl-4H-1,3-benzodioxin

This compound is prepared according to the method of H.E. KATZ and D. J. CRAM (J. Am. Chem. Soc.,

6

1-Bromo-2,6-dimethoxy-3-methoxymethylbenzene

6.a

3-Bromo-2-hydroxy-4-methoxybenzenemethanol 28 g (0.12 mole) of methyl 3-bromo-2-hydroxy-4-methoxybenzoate (prepared according to the method of T. M. CRESP et al., J. Chem. Soc. Perkin Trans., Part 1, (1973), 340–345) dissolved in 250 ml of tetrahydrofuran, are added dropwise, in the course of 75 minutes, at 0° C. to a suspension of 6.06 g (0.159 mole) oflithium aluminum hydride in 100 ml of tetrahydrofuran. The reaction mixture is stirred for 3 hours at ambient temperature. Subsequently, there is added a mixture of 11.5 ml of water and 12 ml of tetrahydrofuran, followed by acifification with 28.6 ml of concentrated hydrochloric acid dissolved in 300 ml of water. The mixture is extracted with dichloromethane. The organic phases are washed with water, dried over anhydrous sodium sulfate and then evaporated pressure. The residue (22.9 g) is used as such in the following step. Yield: 91% of theory.

NMR (CDCl$_3$): delta 3.88 (3H, s, OCH$_3$), 6.45 (1H, d, J=8.6 Hz, ArH), 7.1 (1H, d, J=8.6 Hz, ArH).

6.b

2-Bromo-3-methoxy-6-methoxymethylphenol

A mixture of 22.8 g of 3-bromo-2-hydroxy-4-methoxybenzenemethano, 230 ml of 2,2-dimethoxypropane and 23 g of montmorillonite K10 (freshly dehydrated by azeotropic distillation with toluene) in 200 ml of toluene is stirred at ambient temperature for 90 minutes. After filtration and removal of the solvent, 24.1 g of 2-bromo-3-methoxy-6-methoxymethylphenol are obtained, which can be recrystallized from diisopropyl ether. Yield: 99% of theory; M.P.: 98°–100° C.

| Analysis for C$_9$H$_{11}$BrO$_3$ in %: | | | |
|---|---|---|---|
| calc.: | C 43.72 | H | 4.45 |
| found: | 44.32 | | 4.49 |

6.c

1-Bromo-2,6-dimethoxy-3-methoxymethylbenzene 24.1 g (0.098 mole) of 2-bromo-3-methoxy-6-methoxymethylphenol and 27.7 g of methyl iodide are dissolved in 200 ml of acetone in the presence of 14.82 g (0.107 mole) of potassium carbonate. This solution is heated at reflux temperature, with stirring, for 2.5 hours. It is then cooled, the mineral salts are filtered off and the filtrate is distilled to remove the acetone. The residue is taken up in water and extracted with dichloromethane. The organic phase is dried over anhydrous sodium sulfate and distilled under reduced pressure. 13.1 g of 1-bromo-2,6-dimethoxy-3-methoxymethylbenzene are obtained. Yield: 51% of theory; B.P.: 92°–115° C./0.005 mbar.

NMR (CDCl$_3$): delta 3.4 (3H, s, OCH$_3$), 3.88 (3H, s, OCH$_3$), 3.9 (3H, s, OCH$_3$), 4.48 (2H, s, CH$_2$), 6.74 (1H, s, J=8.6 Hz, ArH), 7.33 (1H, d, J=8.6 Hz, ArH).

7

1-Bromo-2,6-dimethoxy-3-(1-methoxyethyl)benzene

7.a

3-Bromo-2-hydroxy-4-methoxy-alpha-methylbenzenemethanol 64.3 g (0.262 mole) of 3'-bromo-2'-hydroxy-4'-methoxyacetophenone (prepared according to the method of T. M. CRESP et al., J. Chem. Soc. Perkin Trans., Part 1, (1973), 340–345) dissolved in 560 ml of tetrahydrofuran, are added dropwise in the course of 80 minutes and at a temperature of from 13° to 18° C. to a suspension of 13.89 g (0.367 mole) of sodium borohydride in 300 ml of tetrahydrofuran. Thereafter, stirring is continued for 2 hours at ambient temperature. The reaction mixture is decomposed by the addition of 140 ml of tetrahydrofuran containing 3 ml of water, then 60 ml of water are added again thereto. The mixture is acidified by the addition of 415 ml of a 1N aqueous solution of hydrochloric acid. The tetrahydrofuran is removed under reduced pressure and the aqueous phase is extracted 4 times with dichloromethane. The organic phases are dried over anhydrous sodium sulfate and then distilled. The residue obtained (70 g) is used as such in the following step.

7.b

2-Bromo-3-methoxy-6-(1-methoxyethyl)phenol

This compound is prepared by the method described in 6.b. above starting from 65 g of 3-bromo-2-hydroxy-4-methoxy-alpha-methylbenzenemethanol obtained in the preceding step. The crude product, obtained in quantitative yield, is used as such in the following step.

NMR (CDCl$_3$): delta 1.48 (3H, d, J=6.6 Hz, CH$_3$), 3.35 (3H, s, OCH$_3$), 3.88 (3H, s, OCH$_3$), 4.54 (1H, q, J=6.6 Hz, CH), 6.48 (1H, d, J=8.6 Hz, ArH), 7.02 (1H, d, J=8.6 Hz, ArH).

7.c

1-Bromo-2,6-dimethoxy-3-(1-methoxyethyl)benzene

This compound is prepared by the method described in 6.c. above starting from 2-bromo-3-methoxy-6-(1-methoxyethyl)phenol isolated in the preceding step. 56 g of 1-bromo-2,6-dimethoxy-3-(1-methoxyethyl)benzene are obtained. Yield: 77% of theory; B.P.: 95°–120° C./0.001 mbar.

NMR (CDCl$_3$): delta 1.42 (3H, d, H=6.6 Hz, CH$_3$), 3.23 (3H, s, OCH$_3$), 3.88 (3H, s, OCH$_3$), 3.90 (3H, s, OCH$_3$), 4.68 (1H, q, J=6.6 Hz, CH), 6.79 (1H, d, J=8.6 Hz, ArH), 7.38 (1H, d, J=8.6 Hz, ArH).

B

Preparation of 4-(R$_3$-CO)-1H-imidazoles of formula VI

1

1-Triphenylmethyl-1H-imidazole-4-carboxaldehyde

1.a

1-Triphenylmethyl-1H-imidazole-4-methanol

This compound is prepared according to the method described by J. L. KELLEY et al., (J. Med. Chem., 20, (1977), 721–723). Yield: 71.3% of theory; M.P.: 236° C.

1.b

1-Triphenylmethyl-1H-imidazole-4-carboxaldehyde

This compound is also prepared according to the method of J. L. KELLEY et al. (loc. cit.), the yield being 87.5% of theory; M.P.: 190°–198° C.

2

1-Methyl-1H-imidazole-4-carboxaldehyde

This compound is prepared according to the method of G. LINDGREN et al. (J. Het. Chem., 17, (1980), 679).

3

5-Methyl-1-triphenylmethyl-1H-imidazole-4-carboxyaldehyde

3.a

5-Methyl-1H-imidazole-4-methanol

This compound is prepared according to the method described in Belgian Pat. No. 878,490, the yield being 59.3% of theory.

3.b

5-Methyl-1-triphenylmethyl-1H-imidazole-4-methanol 230 ml (1.659 mole) of triethylamine are added in the course of 15 minutes to a solution of 100 g (0.673 mole) of 5-methyl-1H-imidazole-4-methanol in 1.5 liter of dimethylformamide maintained between 10° and 14° C. Subsequently, a solution containing 192 g (0.69 mole) of triphenylmethyl chloride in 2 liters of dimethylformamide is introduced between 8° and 11° C. The reaction mixture is stirred for 2 hours and then poured on 14 liters of ice. Stirring is continued for 1 hour, whereafter the precipitate obtained is filtered off, washed with 6 liters of water and dried. This precipitate is then again taken up in 4 liters of boiling ethanol and the insoluble material is separated by hot filtration. Thus, a first crop (19 g; M.P.: 255°–260° C.) of the desired product is recovered. The alcoholic filtrate is filtered hot on Norit, then concentrated and cooled while stirring. A second crop of the desired product crystallizes. It is filtered off, the yield being 28.3 g; M.P.: 255°–262° C. Finally, the filtrate is distilled under reduced pressure and the residue obtained is dissolved in 1 liter of a 95:5 v/v dichloromethane-methanol mixture and the solution obtained is purified by passage through a column of 1.8 kg of silica (0.2–0.5 mm) (eluent: a 80:20 v/v dichloromethane-methanol mixture). A further 72.1 g of the desired product are thus recovered. In total, 119.4 g are recovered containing practically only one of the two possible isomers in the 4- and 5-positions, namely, the 5-methyl-1-triphenylmethyl-1H-imidazole-4-methanol. The yield is 50.1% of theory. The product obtained is used as such in the following step.

3.c

5-Methyl-1-triphenylmethyl-1H-imidazole-4-carboxaldehyde

A solution of 19 g (0.0536 mole) of the product from the preceding step in 400 ml of chloroform is heated under reflux for 85 minutes in the presence of 32.65 g (0.375 mole) of manganese dioxide. The manganese salts are eliminated by filtration over Dicalite and the filtrate is distilled. The residue is recrystallized from 200 ml of ethyl acetate. A first crop of 4.37 g of the desired product is obtained. A second crop of 9.43 g is further obtained after concentration of the mother liquors to a volume of 60 ml and crystallization. Yield: 73.5% of theory; M.P.: 195°–196° C. The product obtained contains only one position isomer.

| Analysis for $C_{24}H_{20}N_2O$ in %: | | | | | | |
|---|---|---|---|---|---|---|
| calc.: | C | 81.18 | H | 5.68 | N | 7.95 |
| found: | | 81.37 | | 6.25 | | 7.95 |

4

1-(1-Triphenylmethyl-1H-imidazol-4-yl)-1-ethanone

4.a alpha-Methyl-1-triphenylmethyl-1H-imidazole-4-methanol

This compound is prepared according to the method of J. L. KELLEY et al. (J. Med. Chem., 20, (1977), 721–723).

4.b

1-(1-Triphenylmethyl-1H-imidazol-4-yl)-1-ethanone

A mixture of 221.3 g (2.544 moles) of manganese dioxide and 56.9 g (0.161 mole) of alpha-methyl-1-triphenylmethyl-1H-imidazole-4-methanol dissolved in 2.5 liters of chloroform is heated under reflux for 90 minutes. The solution is then cooled to about 50° C., filtered and the chloroform is eliminated by distillation. The residue is dissolved in 400 ml of isopropyl alcohol and filtered hot on Norit. The product crystallizes upon cooling. There are obtained 32.8 g of 1-(1-triphenylmethyl-1H-imidazol-4-yl)-1-ethanone. Yield: 58% of theory; M.P.: 158°–160° C.

| Analysis for $C_{24}H_{20}N_2O$ in %: | | | | | | |
|---|---|---|---|---|---|---|
| calc.: | C | 81.82 | H | 5.68 | N | 7.95 |
| found: | | 81.89 | | 5.65 | | 7.90 |

5

1-(1-Triphenylmethyl-1H-imidazol-4-yl)-1-pentanone

5.a alpha-n-Butyl-1-triphenylmethyl-1H-imidazole-4-methanol

A solution of 0.22 mole of n-butyl magnesium bromide in 75 ml of tetrahydrofuran is slowly added, under an atmosphere of argon, to 67.6 g (0.2 mole) of 1-triphenylmethyl-1H-imidazole-4-carboxaldehyde (obtained as described in 1.b. above) in 500 ml of tetrahydrofuran. The temperature of the mixture is maintained at about 20° C. by cooling on an ice-bath. When the addition is complete, stirring is maintained for 30 minutes at ambient temperature and then 11 g of ammonium chloride and 100 ml of water are successively added. The mixture is extracted with dichloromethane. The organic phases are dried over anhydrous sodium sulfate, then evaporated under reduced pressure. The residue is recrystallized from a 2:1 v/v ethyl acetate-diethyl ether mixture. 45.8 g of alpha-n-butyl-1-triphenylmethyl-1H-imidazole-4-methanol are obtained. Yield: 58% of theory; M.P.: 119°–120° C.

| Analysis for $C_{27}H_{28}N_2O$ in %: | | | | | | |
|---|---|---|---|---|---|---|
| calc.: | C | 81.82 | H | 7.07 | N | 7.07 |
| found: | | 79.13 | | 6.82 | | 6.65 |

5.b

1-(1-Triphenylmethyl-1H-imidazol-4-yl)-1-pentanone

This compound is prepared by the method described in 4.b. above, starting from alpha-n-butyl-1-triphenylmethyl-1H-imidazole-4-methanol obtained in the preceding step.

The oily residue obtained after evaporation of the chloroform is purified by chromatography on silica (eluent: dichloromethane). 39 g of 1-(1-triphenylmethyl-1H-imidazol-4-yl)-1-pentanone are obtained. Yield: 85.3% of theory; M.P.: 115°–118° C.

| Analysis for $C_{27}H_{26}N_2O$ in %: | | | | | | |
|---|---|---|---|---|---|---|
| calc.: | C | 82.23 | H | 6.60 | N | 7.11 |
| found: | | 82.18 | | 6.61 | | 7.14 |

C

Reaction of an organometallic derivative of formula V with 4-($R_3$-CO)-1H-imidazoles of formula VI

1 alpha-(6-Chloro-4H-1,3-benzodioxin-8-yl)-1-triphenylmethyl-1H-imidazole-4-methanol 121 g (0.485 mole) of 8-bromo-6-chloro-4H-1,3-benzodioxin, dissolved in 400 ml of dry tetrahydrofuran, are added dropwide, under an atmosphere of nitrogen, to a suspension of 12.16 g (0.5 mole) of magnesium in 430 ml of anhydrous tetrahydrofuran maintained under reflux.

When the addition is complete, reflux is maintained for 30 minutes and the mixture is cooled to about 40 C. The organomagnesium compound thus formed is added rapidly to 164 g (0.485 mole) of 1-triphenylmethyl-1H-imidazole-4-carboxaldehyde dissolved in 2 liters of tetrahydrofuran preheated to 40° C.

The temperatures increases to 50° C. during the course of the addition. Stirring is maintained for 1 hour at 40° C. The reaction mixture is then cooled to 0° C. and decomposed by the addition of 1 liter of a saturated aqueous solution of ammonium chloride. The precipitate formed is filtered off and washed with methanol and with diethyl ether. 140.7 g of product are thus recovered. The product is further purified by stirring in 1 liter of water. It is filtered off, washed with ethanol and then with diethyl ether. 121.3 g of alpha-(6-chloro-4H-1,3-benzodioxin-8-yl)-1-triphenylmethyl-1H-imidazole-4-methanol are obtained. Yield: 49.2% of theory; M.P.: 233°–235° C.

| Analysis for $C_{31}H_{25}ClN_2O_3$ in %: | | | | | | |
|---|---|---|---|---|---|---|
| calc.: | C | 73.15 | H | 4.91 | N | 5.50 |
| found: | | 73.21 | | 4.94 | | 5.48 |

2 alpha-(4H-1,3-Benzodioxin-6-yl)-1-triphenylmethyl-1H-imidazole-4-methanol

This compound is prepared like the preceding compound but starting from 6-bromo-4H-1,3-benzodioxin and 1-triphenylmethyl-1H-imidazole-4-carboxaldehyde. After decomposing the reaction mixture, the reaction product is extracted with dichloromethane and recrystallized from isopropyl alcohol. By chromatography of the residue obtained after evaporation of the mother liquors, there is obtained a second crop of product. Yield: 53% of theory; M.P.: 165°–167° C.

| Analysis for $C_{31}H_{26}N_2O_3$ in %: | | | | | | |
|---|---|---|---|---|---|---|
| calc.: | C | 78.48 | H | 5.48 | N | 5.91 |
| found: | | 78.19 | | 5.82 | | 5.84 |

3 alpha-(6-Chloro-2,2-dimethyl-4H-1,3-benzodioxin-8-yl)-1-triphenylmethyl-1H-imidazole-4-methanol 2 ml of dibromoethane are added to a suspension of 26.73 g (1 mole + 10% excess) of magnesium in 250 ml of anhydrous tetrahydrofuran and warmed to about 30° C. to initiate the reaction. Immediately thereafter, 277.5 g (1 mole) of 8-bromo-6-chloro-2,2-dimethyl-4H-1,3-benzodioxin dissolved in 250 ml of tetrahydrofuran are added dropwise thereto in such a manner that the temperature does not exceed 40° C. The addition takes about 150 minutes. The organomagnesium compound is cooled to about 10° C. (partial precipitation) and it is then added to a solution of 338 g (1 mole) of 1-triphenylmethyl-1H-imidazole-4-carboxaldehyde in 2.8 liters of tetrahydrofuran which has previously been cooled to 0° C. During the addition, the temperature of the mixture increases progressively to 20° C. Stirring is continued for 1 hour at this temperature and then 53.5 g (1 mole) of ammonium chloride are added. After stirring for 1 hour, 18 ml of water are added and stirring is maintained for a further hour. The tetrahydrofuran is removed under reduced pressure. The residue is taken up in 5 liters of dichloromethane and washed with 2 liters of water containing 30 g of sodium bisulfite. The aqueous phase is separated and washed with 1 liter of dichloromethane. The organic phases are again washed with water, then dried over anhydrous sodium sulfate and the solvent removed under reduced pressure. The residue is recrystallized from about 4 liters of toluene at 80° C. and filtered hot on Norit. 335.6 g of alpha-(6-chloro-2,2-dimethyl-4H-1,3-benzodioxin-8-yl)-1-triphenylmethyl-1H-imidazole-4-methanol, which contans one molecule of toluene, are thus obtained. M.P.: 120° C. followed by 188° C.

| Analysis for $C_{33}H_{29}ClN_2O_3 + C_7H_8$ in %: | | | | | | |
|---|---|---|---|---|---|---|
| calc.: | C | 76.81 | H | 5.78 | N | 4.37 |
| found: | | 74.78 | | 5.24 | | 4.73 |

The following compounds are prepared by the method described under 3. above.

4 alpha-(6-Chloro-2,2-dimethyl-4H-1,3-benzodioxin-8-yl)-1-methyl-1H-imidazole-4-methanol Starting from 8-bromo-6-chloro-2,2-dimethyl-4H-1,3-benzodioxin and 1-methyl-1H-imidazole-4-carboxaldehyde. The addition of the organomagnesium compound is carried out at 0° C. Yield: 63.5% of theory; M.P.: 131°–136° C. (recrystallized from ethyl acetate).

Analysis for $C_{17}H_{17}ClN_2O_3$ in %:

| | C | H | N | Cl |
|---|---|---|---|---|
| calc.: | 58.35 | 5.51 | 9.08 | 11.55 |
| found: | 58.47 | 5.54 | 8.97 | 11.49 |

5 alpha-(6-Chloro-2,2-dimethyl-4H-1,3-benzodioxin-8-yl)-5-methyl-1-triphenylmethyl-1H-imidazole-4-methanol Starting from 8-bromo-6-chloro-2,2-dimethyl-4H-1,3-benzodioxin and 5-methyl-1-triphenylmethyl-1H-imidazole-4-carboxaldehyde. The addition of the organomagnesium compound is carried out at 0° C. Yield: 50% of theory;

M.P.: 100°–120° C. (recrystallized from acetonitrile).

NMR (CDCl₃): delta 1.4 (6H, m, CH₃—C—CH₃), 1.94 (3H, s, CH₃), 4.79 (2H, s, CH₂), 5.98 (1H, s, CHOH), 6.65–7.70 (18H, m, ArH+ImH).

6 alpha-(2,2,6-Trimethyl-4H-1,3-benzodioxin-8-yl)-1-triphenylmethyl-1H-imidazole-4-methanol Starting from 8-bromo-2,2,6-trimethyl-4H-1,3-benzodioxin and 1-triphenylmethyl-1H-imidazole-4-carboxaldehyde. The organomagnesium compound is added at ambient temperature. The reaction product is purified by chromatography on silica (15 μm) (eluent: 98:2 v/v dichloromethanemethanol). Yield: 31% of theory; M.P.: 205°–215° C. (recrystallized from acetonitrile).

NMR (CDCl₃): delta 1.3 (3H, s, CH₃—C—CH₃), 1.38 (3H, s, CH₃—C—CH₃), 2.21 (3H, s, CH₃), 4.78 (2H, s, CH₂), 6.02 (1H, broad s, CHOH), 6.72 (2H, m, ImH+OH), 7.0–7.65 (18H, m, ArH+ImH).

7 alpha-(2,2-Dimethyl-4H-1,3-benzodioxin-6-yl)-1-triphenylmethyl-1H-imidazole-4-methanol Starting from 6-bromo-2,2-dimethyl-4H-1,3-benzodioxin and 1-triphenylmethyl-1H-imidazole-4-carboxaldehyde. The temperature of the reaction mixture does not exceed 40° C. Yield: 54.5% of theory; M.P.: 155°–162° C. (recrystallized from acetonitrile).

NMR (DMSO): delta 1.43 (6H, s, CH₃—C—CH₃), 4.77 (2H, s, CH₂), 5.53 (2H, s, CH and OH), 6.6–7.7 (20H, m, ArH+ImH).

8 alpha-(2,6-Dimethoxy-3-methoxymethylphenyl)-1-triphenylmethyl-1H-imidazole-4-methanol Starting from 1-bromo-2,6-dimethoxy-3-methoxymethylbenzene and 1-triphenylmethyl-1H-imidazole-4-carboxaldehyde. The reaction product is purified by chromatography on silica and is present in the form of a glassy lac. Yield: 48% of theory.

NMR (CDCl₃): delta 3.36 (3H, s, OCH₃), 3.7 (6H, s, 2×OCH₃), 4.43 (2H, s, CH₂), 6.0–6.4 (1H, m, CH), 6.5–7.6 (20H, m, ArH+ImH+OH).

9 alpha-[2,6-Dimethoxy-3-(1-methoxyethyl)phenyl]-1-triphenylmethyl-1H-imidazole-4-methanol Starting from 1-bromo-2,6-dimethoxy-3-(1-methoxyethyl)benzene and 1-triphenylmethyl-1H-imidazole-4-carboxaldehyde. The reaction product is purified by chromatography on silica (eluent: 98:2 v/v dichloromethanemethanol). Yield: 49.7% of theory; M.P.: 96°–99° C. (recrystallized from acetonitrile).

Analysis for $C_{34}H_{34}N_2O_4$ in %:

| | C | H | N |
|---|---|---|---|
| calc.: | 76.4 | 6.36 | 5.24 |
| found: | 76.37 | 6.31 | 5.29 |

10 alpha-(6-Chloro-2,2-dimethyl-4H-1,3-benzodioxin-8-yl)-alpha-methyl-1-triphenylmethyl-1H-imidazole-4-methanol The organomagnesium compound of 8-bromo-6-chloro-2,2-dimethyl-4H-1,3-benzodioxin is prepared as described in 3. above. Then, in 20 minutes and at a temperature not exceeding 25° C., there are added 15 g (0.0426 mole) of this organomgnesium compound to 15 g (0.0426 mole) of 1-(1-triphenylmethyl-1H-imidazol-4-yl)-1-ethanone dissolved in 150 ml of tetrahydrofuran. The reaction mixture is stirred for 165 minutes and then decomposed with 2.5 g of ammonium chloride dissolved in 50 ml of water. It is extracted with dichloromethane; the organic phase is dried over anhydrous sodium sulfate and then distilled. The residue is purified by chromatography on silica (eluent: 98:2 v/v dichloromethane-methanol). 5.68 g of alpha-(6-chloro-2,2-dimethyl-4H-1,3-benzodioxin-8-yl)-alpha-methyl-1-triphenylmethyl-1H-imidazole-4-methanol are obtained; M.P.: 182°–184° C. (recrystallized from ethyl acetate). This compound is idential with that prepared in Example 2.B.2.

11 alpha-n-Butyl-alpha-(6-chloro-2,2-dimethyl-4H-1,3-benzodioxin-8-yl)-1-triphenylmethyl-1H-imidazole-4-methanol This compound is prepared like the preceding compound by reacting the organomagnesium compound of 8-bromo-6-chloro-2,2-dimethyl-4H-1,3-benzodioxin with 1-(1-triphenylmethyl-1H-imidazol-4-yl)-1-pentanone. Yield: 54.6% of theory; M.P.: 124° C. (recrystallized from petroleum ether).

NMR (CDCl₃): delta 0.6–3.3 (15H, m, C₄H₉ and CH₃—C—CH₃), 4.26 (1H, broad s, OH), 4.78 (2H, s, CH₂), 6.7–8.0 (19H, m, ArH+ImH).

12 alpha-(2,2-Dimethyl-4H-1,3-benzodioxin-8-yl)-1-methyl-1H-imidazole-4-methanol hydrochloride 15.88 g of alpha-(6-chloro-2,2-dimethyl-4H-1,3-benzodioxin-8-yl)-1-methyl-1H-imidazole-4-methanol (prepared as in 4. above), dissolved in 160 ml of methanol, are subjected to hydrogenolysis in the presence of 3 g of 10% palladium on carbon under a hydrogen pressure of 3.5 bars at 50° C. for 150 minutes. The catalyst is then filtered off, the solvent is removed and the residue is stirred in diethyl ether. The ethereal phase is decanted off and the residue obtained is used as such in the following step.

EXAMPLE 2

Preparation of starting compounds of formula II ($R_6$=H, $R_7$=$C_1$-$C_4$-alkyl or triphenylmethyl) by method (b)

A

Preparation of ketones of formula VII

1

(6-Chloro-4H-1,3-benzodioxin-8-yl)(1-triphenylmethyl-1H-imidazol-4-yl)ketone

This compound is prepared according to the process described in Example 1.B.4.b. starting from alpha-(6-chloro-4H-1,3-benzodioxin-8-yl)-1-triphenylmethyl-1H-imidazole-4-methanol (prepared as Example 1.C.1). Yield: 95% of theory; M.P.: 175°–182° C. A sample recrystallized from ethanol melts at 182°–185° C. and 203° C.

| Analysis for $C_{31}H_{23}ClN_2O_3$ in %: | | | | | | | | | |
|---|---|---|---|---|---|---|---|---|---|
| calc.: | C | 73.45 | H | 4.54 | N | 5.53 | Cl | 7.01 |
| found: | | 72.48 | | 4.48 | | 5.18 | | 6.96 |

2

(6-Chloro-2,2-dimethyl-4H-1,3-benzodioxin-8-yl)(1-triphenylmethyl-1H-imidazol-4-yl)ketone This compound is prepared according to the process described in Example 1.B.4.b. starting from alpha-(6-chloro-2,2-dimethyl-4H-1,3-benzodioxin-8-yl)-1-triphenylmethyl-1H-imidazole-4-methanol (prepared in Example 1.C.3). Yield: 88% of theory (practically pure product); M.P.: 200°–205° C.

| Analysis for $C_{33}H_{27}ClN_2O_3$ in %: | | | | | | | | | |
|---|---|---|---|---|---|---|---|---|---|
| calc.: | C | 74.08 | H | 5.05 | N | 5.24 | Cl | 6.64 |
| found: | | 74.17 | | 5.03 | | 5.22 | | 6.73 |

B

Reaction of a ketone of formula VII with an organomagnesium compound of formula VIII

1 alpha-(6-Chloro-4H-1,3-benzodioxin-8-yl)-alpha-methyl-1-triphenylmethyl-1H-imidazole-4-methanol A suspension of 0.148 mole of methyl magnesium iodide in 150 ml of diethyl ether at a temperature of 30° C., is added at ambient temperature to 17.3 g (0.033 mole) of (6-chloro-4H-1,3-benzodioxin-8-yl)(1-triphenylmethyl-1H-imidazol-4-yl)ketone dissolved in 200 ml of tetrahydrofuran. The temperature of the reaction mixture increases to 40° C. When the addition is complete, stirring is maintained for 1 hour at ambient temperature. There is then added 8 g of ammonium chloride and stirring is continued for a further hour. Subsequently, 100 ml of water are added and the reaction mixture is extracted twice with dichloromethane. The organic phases are dried over anhydrous sodium sulfate and the solvent is removed under reduced pressure. The residue is recrystallized from 100 ml of ethyl acetate. 13.77 g of alpha-(6-chloro-4H-1,3-benzodioxin-8-yl)-alpha-methyl-1-triphenylmethyl-1H-imidazole-4-methanol are obtained. Yield: 80% of theory; M.P.: 248°–250° C. (decomposition).

| Analysis for $C_{32}H_{27}ClN_2O_3$ in %: | | | | | | | | | |
|---|---|---|---|---|---|---|---|---|---|
| calc.: | C | 73.49 | H | 5.16 | N | 5.36 | Cl | 6.7 |
| found: | | 73.41 | | 5.05 | | 5.26 | | 6.93 |

2 alpha-(6-Chloro-2,2-dimethyl-4H-1,3-benzodioxin-8-yl)-alpha-methyl-1-triphenylmethyl-1H-imidazole-4-methanol This compound is prepared like the preceding compound starting from methyl magnesium iodide and (6-chloro-2,2-dimethyl-4H-1,3-benzodioxin-8-yl)(1-triphenylmethyl-1H-imidazol-4-yl)ketone. The residue obtained after evaporation of the dichloromethane crystallizes when stirred in diethyl ether. Yield: 80% of theory; M.P.: 182°–184° C. (recrystallized from ethyl acetate).

| Analysis for $C_{34}H_{31}ClN_2O_3$ in %: | | | | | | | | | |
|---|---|---|---|---|---|---|---|---|---|
| calc.: | C | 74.11 | H | 5.63 | N | 5.08 | Cl | 6.45 |
| found: | | 73.98 | | 5.65 | | 5.00 | | 6.49 |

This compound is identical with that prepared in Example 1.C.10.

EXAMPLE 3

Preparation of starting of formula II ($R_6$=H or $C_1$-$C_4$-alkyl, $R_7$=H)

1

4-[(2,2-Dimethyl-4H-1,3-benzodioxin-8-yl)(methoxy)-methyl]-1H-imidazole hydrochloride and alpha-(2,2-dimethyl-4H-1,3-benzodioxin-8-yl)-1H-imidazole-4-methanol hydrochloride 125.4 g (0.23 mole) of alpha-(6-chloro-2,2-dimethyl-4H-1,3-benzodioxin-8-yl)-1-triphenylmethyl-1H-imidazole-4-methanol (prepared in Example 1.C.3.), partly dissolved in 1250 ml of methanol, are subjected to hydrogenolysis in the presence of 6 g of 10% palladium on carbon under an initial hydrogen pressure of 2.7 bars. The reaction is carried out at a temperature of 60° C. The catalyst is then filtered off on Hyflo-cel and the methanol is removed under reduced pressure. The residue is taken up in 100 ml of methanol and cooled on an ice-bath. The triphenylmethane which has crystallized is filtered off and the filtrate is evaporated. The residue obtained is stirred for at least 12 hours in 650 ml of diethyl ether. The precipitate is filtered off and washed with diethyl ether. There are obtained 64.59 g of an amorphous powder consisting of a mixture of the desired alcohol and the O-methyl derivative in the proportion of 35:65, determined by NMR. This mixture is used as such in the following step.

A 5.36 g sample of this mixture of products is recrystallized from 20 ml of a 1:1 v/v ethanol-diethyl ether mixture. 1.35 g of pure alpha-(2,2-dimethyl-4H-1,3-benzodioxin-8-yl)-1H-imidazole-4-methanol hydrochloride is isolated. This product does not have a sharp melting point (decomposition).

| Analysis for $C_{14}H_{16}N_2O_3 \cdot HCl$ in %: | | | | | | | |
|---|---|---|---|---|---|---|---|
| calc.: | C | 56.66 | H | 5.40 | N | 9.44 | Cl— 11.97 |
| found: | | 55.81 | | 5.77 | | 8.94 | 11.83 |

The O-methyl derivative formed in the course of the hydrogenolysis is separated from the reaction mixture, neutralized by the addition of ammonia and at the same time purified by chromatography. The 4-[(2,2-dimethyl-4H-1,3-benzodioxin-8-yl)(methoxy)methyl]-1H-imidazole obtained is converted into the hydrochloride by the addition of a solution of hydrogen chloride in methanol. M.P.: 150°–155° C. (decomposition).

| Analysis for $C_{15}H_{18}N_2O_3 \cdot HCl$ in %: | | | | | | | |
|---|---|---|---|---|---|---|---|
| calc.: | C | 57.97 | H | 6.12 | N | 9.02 | Cl— 11.43 |
| found: | | 58.12 | | 6.08 | | 9.10 | 11.40 |

2 alpha-(2,2-Dimethyl-4H-1,3-benzodioxin-8-yl)-5-methyl-1H-imidazole-4-methanol hydrochloride and 4-[(2,2-dimethyl-4H-1,3-benzodioxin-8-yl)(methoxy)methyl]-5-methyl-1H-imidazole hydrochloride 17.5 g (0.032 mole) of alpha-(6-chloro-2,2-dimethyl-4H-1,3-benzodioxin-8-yl)-5-methyl-1-triphenylmethyl-1H-imidazole-4-methanol (prepared in Example 1.C.5.), dissolved in 300 ml of methanol, are subjected to hydrogenolysis in the presence of 1.5 g of 10% palladium on carbon under a hydrogen pressure of 3.5 bars at 50° C. for 3 hours. The catalyst is then filtered off, the solvent is removed and the residue is stirred in diethyl ether to remove triphenylmethane. The residue obtained after decanting off the ethereal phase is characterized by its NMR spectrum and is a mixture comprising 65% of the hydrochloride of the O-methyl derivative and 35% of the hydrochloride of the alcohol. This mixture is used as such in the following step.

3

4-[(2,2,6-Trimethyl-4H-1,3-benzodioxin-8-yl)(methoxy)methyl]-1H-imidazole and 4-[(2,2,6-trimethyl-4H-1,3-benzodioxin-8-yl)methyl]-1H-imidazole 9.45 g (0.0183 mole) of alpha-(2,2,6-trimethyl-4H-1,3-benzodioxin-8-yl)-1-triphenylmethyl-1H-imidazole-4-methanol (prepared in Example 1.C.6.), dissolved in 300 ml of methanol, are subjected to hyrogeolysis in the presence of 0.6 g of 10% palladium on carbon for 4 hours at 80° C., under a hydrogen pressure of 2 hours. The catalyst is then filtered off and the solvent removed. The residue obtained is stirred in diethyl ether to remove the triphenylmethane, then chromatographed on 700 g of silica (10 μm) (eluent: 95:5 v/v dichloromethane-methanol). A 60:40 mixture of 4-[(2,2,6-trimethyl-4H-1,3-benzodioxin-8-yl)(methoxy)methyl]-1H-imidazole and 4-[(2,2,6-trimethyl-4H-1,3-benzodioxin-8-yl)methyl]-1H-imidazole is isolated and identified by NMR by the presence of a peak corresponding to the methoxy radical (DMSO: delta 3.13). The mixture is used as such in the following step.

4 alpha-(2,2-Dimethyl-4H-1,3-benzodioxin-6-yl)-1H-imidazole-4-methanol

The process used is the same as that described under 2. above but starting from alpha-(2,2-dimethyl-4H-1,3-benzodioxin-6-yl)-1-triphenylmethyl-1H-imidazole-4-methanol (prepared in Example 1.C.7.). The residue obtained is chromatographed on silica (15 μm) (eluent: 95:5 v/v dichloromethane-methanol). The alpha-(2,2-dimethyl-4H-1,3-benzodioxin-6-yl)-1H-imidazole-4-methanol isolated is recrystallized from ethyl acetate. M.P.: 96° C.

| Analysis for $C_{14}H_{16}N_2O_3$ in %: | | | | | | |
|---|---|---|---|---|---|---|
| calc.: | C | 64.62 | H | 6.15 | N | 10.77 |
| found: | | 64.37 | | 6.40 | | 10.68 |

5 alpha-(2,2-Dimethyl-4H-1,3-benzodioxin-8-yl)-1H-imidazole-4-methanol 5.75 g (0.25 mole) of sodium are added piece by piece to a suspension of 21.46 g (0.04 mole) of alpha-(6-chloro-2,2-dimethyl-4H-1,3-benzodioxin-8-yl)-1-triphenylmethyl-1H-imidazole-4-methanol (prepared in Example 1.C.3.) in 2 liters of ammonia and 200 ml of toluene. stirring is maintained for 40 minutes, then the reaction mixture is decomposed by the addition of 6.42 g (0.12 mole) of ammonium chloride. 500 ml of toluene containing 10% of methanol are added thereto, the ammonia is evaporated and 500 ml of water are added thereto. The toluene phase is decanted off, dried over anhydrous sodium sulfate and then distilled. The residue, containing triphenylmethane, is partly dissolved in 50 ml of water containing 3.3 ml of concentrated hydrochloric acid and the suspension obtained is extracted with diethyl ether. The aqueous phase is subsequently adjusted to pH 8 by the addition of sodium bicarbonate, then extracted with dichloromethane. Subsequently, the solvent is removed by distillation to give 3.5 g of alpha-(2,2-dimethyl-4H-1,3-benzodioxin-8-yl)-1H-imidazole-4-methanol. Yield: 33% of theory. The product formed a hydrochloride (recrystallizable in a 1:1 v/v ethanol-diethyl ether mixture) which has a glassy appearance and which does not have a sharp melting point.

| Analysis for $C_{14}H_{16}N_2O_3 \cdot HCl$ in %: | | | | | | | |
|---|---|---|---|---|---|---|---|
| calc.: | C | 56.66 | H | 5.40 | N | 9.44 | Cl— 11.97 |
| found: | | 55.81 | | 5.77 | | 8.94 | 11.83 |

6 alpha-(2,6-Dimethoxy-3-methoxymethylphenyl)-1H-imidazole-4-methanol

The process is exactly the same as in 1. above but is performed at 80° C., starting from alpha-(2,6-dimethoxy-3-methoxymethylphenyl)-1-triphenylmethyl-1H-imidazole-4-methanol (prepared in Example 1.C.8.). After removal of the crystallized triphenylmethane and evaporation of the methanol, the residue obtained is purified by chromatography on silica (eluent: 80:20 v/v dichloromethane-methanol). An oil, characterized by its NMR spectrum, is obtained. Yield: 68% of theory.

NMR (CDCl₃): delta 3.38 (3H, s, OCH₃), 3.66 (3H, s, OCH₃), 3.76 (3H, s, OCH₃), 4.43 (2H, s, CH₂), 6.28 (1H, s, CH), 6.69–7.70 (6H, m, ArH+ImH+OH+NH).

7 alpha-[2,6-Dimethoxy-3-(1-methoxyethyl)phenyl]-1H-imidazole-4-methanol

As in 6. above, alpha-[2,6-dimethoxy-3-(1-methoxyethyl)phenyl]-1-triphenylmethyl-1H-imidazole-4-methanol (prepared in Example 1.C.9.) is subjected to hydrogenolysis. Yield: 79.6% of theory; M.P.: 138°–145° C. (recrystallized from tetrahydrofuran-diethyl ether).

| Analysis for C₁₅H₂₀N₂O₄ in %: | | | | | | |
|---|---|---|---|---|---|---|
| calc.: | C | 61.64 | H | 6.85 | N | 9.59 |
| found: | | 61.48 | | 7.0 | | 9.38 |

8 alpha-n-Butyl-alpha-(2,2-dimethyl-4H-1,3-benzodioxin-8-yl)-1H-imidazole-4-methanol The process is exactly the same as 1. above but is performed at 80° C., starting from alpha-n-butyl-alpha-(6-chloro-2,2-dimethyl-4H-1,3-benzodioxin-8-yl)-1-triphenylmethyl-1H-imidazole-4-methanol (prepared in Example 1.C.11.). The residue obtained after filtration of the triphenylmethane and evaporation of the methanol is used as such in the following step.

9 alpha-(2,2-Dimethyl-4H-1,3-benzodioxin-8-yl)-alpha-methyl-1H-imidazole-4-methanol hydrochloride The process is exactly the same as in 2. above but a temperature of 20° C. is used, starting from alpha-(6-chloro-2,2-dimethyl-4H-1,3-benzodioxin-8-yl)-alpha-methyl-1-triphenylmethyl-1H-imidazole-4-methanol (prepared in Example 2.B.2.). The yield is practically quantitative; M.P.: 85°–100° C. (decomposition). An analytical sample is prepared by stirring in diethyl ether; M.P.: 72°–90° C. (decomposition).

| Analysis for C₁₅H₁₈N₂O₃.HCl in %: | | | | | | | | |
|---|---|---|---|---|---|---|---|---|
| calc.: | C | 57.97 | H | 6.12 | N | 9.01 | Cl— | 11.43 |
| found: | | 57.94 | | 6.95 | | 8.12 | | 9.51 |

EXAMPLE 4

Preparation of 1H-imidazoles of formula I
($Z_1=Z_2$=alkyl and $Z_1+Z_2$=—CH₂—)

1

4-[(4H-1,3-benzodioxin-8-yl)methyl]-1H-imidazole hydrochloride 50.85 g (0.1 mole) of alpha-(6-chloro-4H-1,3-benzodioxin-8-yl)-1-triphenylmethyl-1H-imidazole-4-methanol (prepared in Example 1.C.1.), dissolved in 500 ml of acetic acid, are hydrogenolyzed in the presence of 3 g of 10% palladium on carbon for 2 hours at 80° C., under a hydrogen pressure of 2.41 bars. The catalyst is then filtered off and the solvent is distilled under reduced pressure. The residue obtained is extracted three times with diethyl ether to remove the triphenylmethane formed. It is subsequently recrystallized from 50 ml of acetonitrile. 21.2 g of 4-[(4H-1,3-benzodioxin-8-yl)methyl]-1H-imidazole hydrochloride are obtained. Yield: 83% of theory; M.P.: 168°–173° C.

| Analysis for C₁₂H₁₂N₂O₂.HCl in %: | | | | | | | | |
|---|---|---|---|---|---|---|---|---|
| calc.: | C | 57.03 | H | 5.15 | N | 11.09 | Cl— | 14.06 |
| found: | | 57.01 | | 5.20 | | 11.02 | | 13.83 |

2

4-[(4H-1,3-benzodioxin-6-yl)methyl]-1H-imidazole

This compound is prepared like the preceding compound but starting from 25 g (0.052 mole) of alpha-(4H-1,3-benzodioxin-6-yl)-1-triphenylmethyl-1H-imidazole-4-methanol (prepared in Example 1.C.2.). The triphenylmethane formed is removed by extracting several times with hexane and the residue is purified by chromatography on silica (eluent: 95:5 v/v dichloromethane-methanol). The fractions containing the product are evaporated and the residue is taken up in a dilute solution of ammonia in methanol. This solution is distilled and the residue is recrystallized from ethyl acetate. 3.5 g of 4-[(4H-1,3-benzodioxin-6-yl)methyl]-1H-imidazole are obtained. Yield: 31.2% of theory: M.P.: 145° C.

| Analysis for C₁₂H₁₂N₂O₂ in %: | | | |
|---|---|---|---|
| calc.: | C 66.66 | H 5.55 | N 12.96 |
| found: | 66.14 | 5.62 | 12.69 |

3

4-[(2,6-Dimethoxy-3-methoxymethylphenyl)methyl]-1H-imidazole hydrochloride 6.75 g (0.0243 mole) of alpha-(2,6-dimethoxy-3-methoxymethylphenyl)-1H-imidazole-4-methanol (prepared in Example 3.6.), previously dissolved in 200 ml of tetrahydrofuran, are introduced into 1 liter of liquid ammonia. There is first added 1.3 g (0.0243 mole) of ammonium chloride and then, for 30 minutes, 1.12 g (0.0486 mole) of sodium piece by piece. After the sodium has completely disappeared, 1.3 g of ammonium chloride is added and the reaction mixture then stirred for 30 minutes. 300 ml of toluene containing 10 ml of methanol are then added. The ammonia is subsequently evaporated on a water-bath. 100 ml of water are then added and the organic phase is decanted. This is dried over anhydrous sodium sulfate and the solvent is evaporated under reduced pressure. The product obtained is purified by chromatography on silica (eluent: 95:4.5:0.5 v/v/v dichloromethane-methanol-ammonia). 1.81 g of product in the form of a lac, is obtained, the yield being 28.4% of theory. It is dissolved in diisopropyl ether and converted into the hydrochloride by the addition of one equivalent of a solution of hydrochloric acid in isopropyl alcohol; M.P.: 130°–135° C.

| Analysis for C₁₄H₁₈N₂O₃.HCl in %: | | | |
|---|---|---|---|
| calc.: | C 56.28 | H 6.36 | N 9.38 |
| found: | 56.13 | 6.39 | 9.10 |

4

4-[[2,6-Dimethoxy-3-(1-methoxyethyl)phenyl]methyl]-1H-imidazole hydrochloride The procedure is exactly the same as in 3. above but starting from alpha[2,6-dimethoxy-3-(1-methoxyethyl)-phenyl]-1H-imidazole-4-methanol (prepared in Example 3.7.). The oil obtained after evaporation of the toluene is taken up in diethyl ether and converted into the hydrochloride by the addition of a solution of hydrochloric acid in methanol. Yield: 68.5% of theory; M.P.: 168°–170° C.

| Analysis for $C_{15}H_{20}N_2O_3 \cdot HCl$ in %: | | | |
|---|---|---|---|
| calc.: | C 57.6 | H 6.72 | N 8.96 | Cl 11.36 |
| found: | 57.52 | 6.84 | 8.89 | 11.27 |

5

4-[1-(4H, 1,3-benzodioxin-8-yl)ethyl]-1H-imidazole

The procedure is exactly the same as in 1. above but starting from alpha-(6chloro-4-H-1,3-benzodioxin-8-yl)-alpha-methyl-1-triphenylmethyl-1H-imidazole-4-methanol (prepared in Example 2.B.1.). After removal of the triphenylmethane, the residue obtained is dissolved in water and the solution rendered alkaline to pH 8 by the addition of a saturated aqueous solution of sodium carbonate. The precipitate formed is redissolved in dichloromethane. The organic phase is dried over anhydrous sodium sulfate and the solvent is evaporated under reduced pressure. The residue is chromatographed on silica (eluent: 95:4.5:0.5 v/v/v dichloromethane-methanol-ammonia). Yield: 52% of theory; M.P.: 145°–148° C. (recrystallized from ethyl acetate).

| Analysis for $C_{13}H_{14}N_2O_2$ in %: | | | |
|---|---|---|---|
| calc.: | C 67.83 | H 6.09 | N 12.17 |
| found: | 67.68 | 6.11 | 12.10 |

The compound thus obtained is in the form of a racemic mixture. This racemate is separated into its optically active isomers by the following method.

2.47 g (0.0165 mole) of d-tartaric acid dissolved in 33 ml of isopropyl alcohol are added into a hot solution of 7.57 g (0.0329 mole) of racemic 4-[1-(4H-1,3-benzodioxin-8yl)ethyl]-1-H-imidazole in 263 ml of isopropyl alcohol. A flaky precipitate separates. The suspension is stirred for 16 hours at ambient temperature, then the liquid phase is removed by decantation. The residue obtined is taken up in 300 ml of boiling isopropyl alcohol; the insoluble material crystallizes out. The mixture is cooled to 45° C. and is stirred for 4 hours at this temperature. It is then filtered hot (45° C.). 3.21 g of a crystalline salt (hemitartrate) are obtained. M.P.: 164° C.

$[alpha]_D^{25} = +40.8$ (c=1, methanol).

The filtrate resulting from the separation of the crystals will be treated as described under (b) hereinafter.

(a) The crystals obtained above are first recrystallized twice from isopropyl alcohol. M.P.: 178° C. $[alpha]_D^{25} = +53.3$ (c=1, methanol). Then 1 g of this salt is dissolved in 33 ml of water and the solution is rendered alkaline to pH 9.5 by the addition of a 1n aqueous solution of sodium hydroxide. A precipitate is formed, which is filtered off and recrystallized from 1 ml of ethyl acetate. 0.457 g of the dextrorotatory isomer d-4-[1-(4H-1,3-benzodioxin-8-yl)ethyl]-1H-imidazole, is obtained. M.P.: 113.7° C. $[alpha]_D^{25} = +69.8$ (c=1, methanol).

| Analysis for $C_{13}H_{14}N_2O_2$ in %: | | | |
|---|---|---|---|
| calc.: | C 67.83 | H 6.09 | N 12.17 |
| found: | 67.88 | 6.06 | 12.13 |

(b) The filtrate is evaporated under reduced pressure to remove the isopropyl alcohol. The residue obtained is dissolved in water and the solution is rendered alkaline to pH 9.5 by the addition of a 1N aqueous solution of sodium hydroxide. The freed base, which precipitates, is filtered off and then treated in isopropyl alcohol with half an equivalent of l-tartaric acid. The salt obtained, which precipitates, is filtered off and recrystallized from isopropyl alcohol, M.P.: 178° C. $[alpha]_D^{25} = -51.57$ (c=1, methanol).

This salt is then redissolved in water and the solution is rendered alkaline in pH 9.5 by the addition of a 1N aqueous solution of sodium hydroxide. A precipitate is formed, which is filtered off and recrystallized twice from ethyl acetate. 0.296 of the levorotatory isomer l-4-[1-(4H-1,3-benzodioxin-8-yl)ethyl]-1H-imidazole is obtained. M.P.: 114.4° C. $[alpha]_D^{25} = -72.6$ (c=1, methanol).

| Analysis for $C_{13}H_{14}N_2O_2$ in %: | | | |
|---|---|---|---|
| calc.: | C 67.83 | H 6.09 | N 12.17 |
| found: | 67.78 | 6.10 | 12.24 |

6

4-[(6-Methyl-4H-1,3-benzodioxin-8-yl)methyl]-1H-imidazole hydrochloride

This compound is prepared in the same manner. M.P.: 175°–183° C. (decomposition).

| Analysis for $C_{13}H_{14}N_2O_2 \cdot HCl$ in %: | | | |
|---|---|---|---|
| calc.: | C 58.58 | H 5.63 | N 10.51 |
| found: | 56.47 | 5.63 | 9.93 |

EXAMPLE 5

Preparation of 4-[1-[2,2-dimethyl-4H-1,3-benzodioxin-6(or 8)-yl]alkyl]-1H-imidazoles of formulae I and III $(Z_1+Z_2=-C(CH_3)_2-)$

1

4-[2,2-Dimethyl-4H-1,3-benzodioxin-6-yl)methyl]-1H-imidazole 3.4 g (0.013 mole) of alpha-(2,2-dimethyl-4H-1,3-benzodioxin-6-yl)-1H-imidazole-4-methanol (prepared in Example 3.4.) are hydrogenolyzed in methanol at 80° C. for 5 hours in the presence of 10% palladium on carbon and under a hydrogen pressure of 2.8 bars. The catalyst is then filtered off and the solvent is removed under reduced pressure. The residue obtained is chromatographed on silica (eluent: 90:10 v/v dichloromethane-methanol). There are obtained 3 g of 4-[(2,2-dimethyl-4H-1,3-benzodioxin-6-yl)methyl]-1H-imidazole. Yield: 97% of theory; M.P.: 150°–170° C.

NMR (DMSO): delta 1.45 (6H, s, CH₃—C—CH₃), 3.78 (2H, s, CH₂), 4.77 (2H, s, CH₂); 6.5–7.7 (5H, m, ArH+ImH).

2.a

4-[(2,2-Dimethyl-4H-1,3-benzodioxin-8-yl)methyl]-1H-imidazole 94.13 g (0.317 mole) of alpha-(2,2-dimethyl-4H-1,3-benzodioxin-8-yl)-1H-imidazole-4-methanol hydrochloride (prepared in Example 3.1. or 3.5.) are introduced into 1 liter of anhydrous liquid ammonia. The solubilization of the reagent is completed by the addition of 1 liter of tetrahydrofuran. 14.6 g (0.634 mole) of sodium are then added piece by piece. 5 minutes after the sodium has disappeared, 34 g of ammonium chloride are added and the reaction mixture is stirred for 30 minutes. There is then added 1.56 liter of a 10% solution of methanol in toluene. The ammonia is then evaporated on a water-bath. 780 ml of water are then added and the organic phase is separated. The aqueous phase is extracted twice with 500 ml of toluene. The organic phases are combined and washed with 1 liter of water, then dried over anhydrous sodium sulfate and distilled under reduced pressure. The residue obtained is recrystallized from 900 ml of boiling acetone. There are thus obtained 57.8 g of 4-[(2,2-dimethyl-4H-1,3-benzodioxin-8-yl)methyl]-1H-imidazole; M.P.: 160°–170° C. Yield: 74.6% of theory.

| Analysis for $C_{14}H_{16}N_2O_2$ in %: | | | |
|---|---|---|---|
| calc.: | C 68.85 | H 6.56 | N 11.48 |
| found: | 69.15 | 6.70 | 11.53 |

2.b

The same compound is prepared starting from 0.8 g (0.0015 mole) of alpha-(6-chloro-2,2-dimethyl-4H-1,3benzodioxin-8-yl)-1-triphenylmethyl-1H-imidazole-4-methanol (prepared in Example 1.C.3.) and 0.245 g (0.0106 mole) of sodium according to the process described in Example 3.5. The residue obtained after evaporation of the toluene phase is chromatographed on 150 g of silica (10 μm) (eluent: 95:5 v/v ethyl acetate-methanol). There is obtained 123 mg of product identical to the compound obtained in 2.a. above.

The following compounds are prepared by the method described in 2.a. above.

3

4-[(2,2-Dimethyl-4H-1,3-benzodioxin-8-yl)methyl]-1-methyl-1H-imidazole

This compound is prepared starting from alpha-(2,2-dimethyl-4H-1,3-benzodioxin-8-yl)-1-methyl-1H-imidazole-4-methanol hydrochloride (prepared in Example 1.C.12.). The residue obtained is purified by chromatography on silica (eluent: 98:2 v/v dichloromethane-methanol). Yield: 67% of theory; M.P.: 67°–72° C. (recrystallized from diisopropyl ether-hexane).

| Analysis for $C_{15}H_{18}N_2O_2$ in %: | | | |
|---|---|---|---|
| calc.: | C 69.74 | H 7.02 | N 10.84 |
| found: | 69.93 | 7.54 | 10.78 |

4

4-[(2,2-Dimethyl-4H-1,3-benzodioxin-8-yl)methyl]-5-methyl-1H-imidazole

This compound is prepared starting from 9.68 g of a mixture of the hydrochlorides of the O-methyl and alcohol derivatives prepared in Example 3.2. It is purified by chromatography on silica (eluent: 90:10 v/v dichloromethane-methanol). These are obtained 4 g of the desired product; M.P.: 172°–178° C. (recrystallized from dichloromethane).

| Analysis for $C_{15}H_{18}N_2O_2$ in %: | | | |
|---|---|---|---|
| calc.: | C 69.74 | H 7.02 | N 10.84 |
| found: | 67.55 | 6.98 | 10.38 |

5

4-[(2,2,6-Trimethyl-4H-1,3-benzodioxin-8-yl)methyl]-1H-imidazole

This compound is prepared from 2.3 g of the mixture containing the O-methyl derivative prepared in Example 3.3. 0.9 g of the desired product is isolated; M.P.: 152°–155° C. (recrystallized from ethyl acetate).

| Analysis for $C_{15}H_{18}N_2O_2$ in %: | | | |
|---|---|---|---|
| calc.: | C 69.74 | H 7.02 | N 10.84 |
| found: | 69.82 | 7.04 | 10.64 |

6

4-[1-(2,2-Dimethyl-4H-1,3-benzodioxin-8-yl)ethyl]-1H-imidazole

This compound is prepared from alpha-(2,2-dimethyl-4H-1,3-benzodioxin-8-yl)-alpha-methyl-1H-imidazole-4-methanol hydrochloride (prepared in Example 3.9.). The residue obtained after evaporation of the toluene crystallizes by stirring at 60° C. in diisopropyl ether. Yield: 60% of theory; M.P.: 118° and 130° C.

| Analysis for $C_{15}H_{18}N_2O_2$ in %: | | | |
|---|---|---|---|
| calc.: | C 69.76 | H 6.97 | N 10.85 |
| found: | 69.64 | 6.95 | 10.72 |

7

4-[1-(2,2-Dimethyl-4H-1,3-benzodioxin-8-yl)pentyl]-1H-imidazole

This compound is prepared by reduction of alpha-n-butyl-alpha-(2,2-dimethyl-4H-1,3-benzodioxin-8-yl)-1H-imidazle-4-methanol (prepared in Example 3.8.). Yield: 23.6% of theory; M.P.: 108°–112° C. (recrystallized from cyclohexane).

| Analysis for $C_{18}H_{24}N_2O_2$ in %: | | | |
|---|---|---|---|
| calc.: | C 72.0 | H 8.0 | N 9.33 |
| found: | 72.08 | 8.15 | 9.32 |

EXAMPLE 6

Preparation of 3-[1-(1H-imidazol-4-yl)alkyl]-2or 6)-hydroxybenzenemethanols of formula I
($Z_1=Z_2=H$)

1

3-[(1H-imidazol-4-yl)methyl]-2-hydroxybenzenemethanol 82.83 g (0.0339 mole) of 4-[(2,2-dimethyl-4H-1,3-benzodioxin-8-yl)methyl]-1H-imidazole (prepared in Example 5.2.) are suspended in 1645 ml of water (pH 7.9) and dissolved by the addition, over the course of 80 minutes, of 349 ml of a 1N aqueous solution of hydrochloric acid. When this addition is complete, the pH of the solution is 2.5. The reaction mixture is subsequently heated for 1 hour on an oil bath at 120° C. The solution is then cooled, treated with 5 g of Norit and filtered on Hyflo-cel. The solution is subsequently rendered alkaline by the addition of 242.5 ml of a 1N aqueous solution of sodium hydroxide (pH 8.5). The precipitate obtained is filtered off, washed with water and dried. This precipitate is then dissolved in 3.3 liters of ethyl acetate in the presence of Norit and of a few grams of sodium sulfate. The mixture is then filtered, concentrated to a volume of 400 ml and left to crystallize. There are obtained 55.67 g of 3-[(1H-imidazol-4-yl)methyl]-2-hydroxybenzenemethanol. Yield: 80.4% of theory; M.P.: 152°-155° C.

| Analysis for $C_{11}H_{12}N_2O_2$ in %: | | | |
|---|---|---|---|
| calc.: | C 64.69 | H 5.92 | N 13.72 |
| found: | 65.05 | 5.69 | 13.72 |

The following compounds are prepared by the method described above:

2

3-[(1-Methyl-1H-imidazol-4-yl)methyl]-2-hydroxybenzenemethanol

This compound is prepared from 7 g of 4-[(2,2-dimethyl-4H-1,3-benzodioxin-8-yl)methyl]-1-methyl-1H-imidazole (prepared in Example 5.3.). There are obtained 5.6 g of the desired product. Yield: 73% of theory; M.P.: 139°-144° C. (recrystallized from acetonitrile).

| Analysis for $C_{12}H_{14}N_2O_2$ in %: | | | |
|---|---|---|---|
| calc.: | C 66.03 | H 6.46 | N 12.83 |
| found: | 65.81 | 6.65 | 12.55 |

3

3-[(5-Methyl-1H-imidazol-4-yl)methyl]-2-hydroxybenzenemethanol

This compound is prepared from 4 g of 4-[2,2-dimethyl-4H-1,3-benzodioxin-8-yl)methyl]-5-methyl-1H-imidazole (prepared in Example 5.4.). There are obtained 2.7 g of the desired product. Yield: 80% of theory; M.P.: 126°-130° C. (recrystallized from acetonitrile).

| Analysis for $C_{12}H_{14}N_2O_2$ in %: | | | |
|---|---|---|---|
| calc.: | C 66.03 | H 6.46 | N 12.83 |
| found: | 66.25 | 6.44 | 12.76 |

4

3-[(1H-imidazol-4-yl)methyl]-2-hydroxy-5-methylbenzenemethanol

This compound is prepared from 3 g of 4-[(2,2,6-trimethyl-4H-1,3-benzodioxin-8-yl)methyl]-1H-imidazole (prepared in Example 5.5.). 2.4 g of the desired product are obtained. Yield: 95% of theory; M.P.: 170°-175° C. (decomposition).

| Analysis for $C_{12}H_{14}N_2O_2$ in %: | | | |
|---|---|---|---|
| calc.: | C 66.03 | H 6.46 | N 12.83 |
| found: | 62.02 | 6.56 | 12.73 |

5

3-[1-(1H-imidazol-4-yl)ethyl]-2-hydroxybenzenemethanol

This compound is prepared by the hydrolysis of 4-[1-(2,2-dimethyl-4H-1,3-benzodioxin-8-yl)ethyl]-1H-imidazole (prepared in Example 5.6.). Yield: 60% of theory; M.P.: 135°-136° C.

| Analysis for $C_{12}H_{14}N_2O_2$ in %: | | | |
|---|---|---|---|
| calc.: | C 66.03 | H 6.46 | N 12.83 |
| found: | 65.97 | 6.44 | 12.80 |

6

3-[1-(1H-imidazol-4-yl)pentyl]-2-hydroxybenzenemethanol

This compound is prepared by the hydrolysis of 4-[1-(2,2-dimethyl-4H-1,3-benzodioxin-8-yl)pentyl]-1H-imidazole (prepared in Example 5.7.). Yield: 94% of theory; M.P.: 93° C.

| Analysis for $C_{15}H_{20}N_2O_2$ in %: | | | |
|---|---|---|---|
| calc.: | C 69.23 | H 7.69 | N 10.77 |
| found: | 69.30 | 7.70 | 10.81 |

7

3-[(1H-imidazol-4-yl)methyl]-6-hydroxybenzenemethanol

This compound is prepared from 4 g of 4-[(2,2-dimethyl-4H-1,3-benzodioxin-6-yl)methyl]-1H-imidazole (prepared in Example 5.1.). 1.6 g of the desired product is obtained. Yield: 48% of theory; M.P.: 149°-155° C. (decomposition).

| Analysis for $C_{11}H_{12}N_2O_2$ in %: | | | |
|---|---|---|---|
| calc.: | C 64.70 | H 5.88 | N 13.72 |
| found: | 65.11 | 6.11 | 13.45 |

EXAMPLE 7

Preparation of starting alkyl 3-[(1H-imidazol-4-yl)methyl]-2-hydroxybenzoates of formula IV Ethyl 3-[(1H-imidazol-4-yl)methyl]-2-hydroxybenzoate a.

Ethyl 3-[(1H-imidazol-4-yl)methyl]-2-oxo-cyclohexanecarboxylate

A solution of sodium ethoxide is prepared by dissolving 58.2 g (2.53 moles) of sodium in 2 liters of absolute ethanol under an atmosphere of argon. It is cooled to 10° C. and 195.5 g (1.15 mole) of ethyl 2-oxo-cyclohexanecarboxylate are added rapidly with vigorous stirring. The sodium salt precipitates and the mixture is stirred for 1 hour at 20° C., then cooled to −10° C. 193.5 g (1.26 mole) of 4-chloromethyl-1H-imidazole hydrochloride dissoolved in 1 liter of absolute ethanol are added dropwise thereto. The reaction mixture is kept at −10° C. for 1 hour and then allowed to return to ambient temperature and maintained at this temperature for 20 hours, while stirring. 2 liters of solvent are distilled off at atmospheric pressure and a solution of sodium ethoxide, formed by dissolving 79.35 g (3.45 moles) of sodium in 1.2 liter of absolute ethanol, is added thereto at 30° to 40° C. Distillation of the solvent is continued until the temperature of the reaction mixture reaches 100°–105° C. The distillation is then stopped and the reaction mixture is heated under reflux for 10 hours. It is then cooled to ambient temperature and 200 ml of absolute ethanol are added thereto. The mixture is then cooled to −10° C. and 400 ml of a 9.9N methanolic solution of hydrochloric acid are added dropwise thereto. The temperature is allowed to increase to 10° C. The sodium chloride formed is removed by centrifugation. After evaporating the solvent under reduced pressure, there are obtained 180 g of a brown oil. The centrifuged deposit of sodium chloride obtained by the centrifugation is washed twice with 1 liter of dichloromethane. This solvent is subsequently removed under reduced pressure, a further 60 g of oil thus being obtained. The oil is purified by chromatography on silica (column diameter 80 mm; silica Merck TLC 60H 15 μm; eluent: 93:6.5:0.5 v/v/v dichloromethane-ethanol-ammonia). There are finally obtained 138 g of ethyl 3-[(1H-imidazol-4-yl)methyl]-2-oxo-cyclohexanecarboxylate in the form of an oil which slowly solidifies (mixture of diastereoisomers). Yield: 48% of theory.

Ethyl 2-oxo-cyclohexanecarboxylate used as starting material is prepared by the method described by H. R. SNYDER et al., (Organic Synthesis, Coll. Vol. II, (1943), 531–534).

4-chloromethyl-1H-imidazole hydrochloride used as starting material is prepared by the method described by R. A. TURNER et al., (J. Am. Chem. Soc., 71, (1949), 2801–2803).

b

Ethyl 3-[(1H-imidazol-4-yl)methyl]-2-hydroxybenzoate 176 g (56.5 ml; 1.1 mole) of bromine dissolved in 400 ml of glacial acetic acid are added dropwise within 30 minutes, at 17° to 20° C. and under an atmosphere of argon, to a solution containing 37.5 g (0.55 mole) of ethyl 3-[(1H-imidazol-4-yl)methyl]-2-oxo-cyclohexanecarboxylate in 1.5 liter of glacial acetic acid. The reaction mixture is subsequently heated under reflux for 4 hours. The red solution becomes progressively blacker. The mixture is cooled to 20° C. and evaporated under reduced pressure. The residue is taken up in 1.2 liter of 50% aqueous acetic acid. There are then added a spatula tip of anion exchange resin (Amberlite IR 45 acetate), 25 g of 10% palladium on carbon and 25 g of 10% rhodium on carbon and hydrogenolysis is carried out for 150 minutes under a hydrogen pressure of 3.5 bars. The reaction mixture is filtered on Celite and the filtrate is evaporated under reduced pressure. The oil obtained is dissolved in 1 liter of an ice-water mixture and the solution is adjusted to a pH of 8 by the addition of a 2N aqueous sodium hydroxide solution and rapidly extracted 5 times with 400 ml of ethyl acetate. The organic phases are combined, dried over anhydrous magnesium sulfate, filtered and evaporated under reduced pressure. The residue is purified by chromatography on silica (eluent: 93.5:6.0:0.5 v/v/v dichloromethane-ethanol-ammonia). There are obtained 75.9 g of ethyl 3-[(1H-imidazol-4-yl)methyl]-2-hydroxybenzoate in the form of an oil which crystallizes slowly. Yield: 55% of theory; M.P.: 133° C.

| Analysis for $C_{13}H_{14}N_2O_3$ in %: | | | |
|---|---|---|---|
| calc.: | C 63.41 | H 5.69 | N 11.38 |
| found: | 63.72 | 5.80 | 11.32 |

EXAMPLE 8

Preparation of 3-[(1H-imidazol-4-yl)methyl]-2-hydroxybenzenemethanols of formula I ($Y_1=OZ_2$, $Y_2=Z_1=Z_2=R_5=H$)

3-[(1H-Imidazol-4-yl)methyl)]-2-hydroxybenzenemethanol 22.8 g (0.6 mole) of lithium aluminum hydride are added in small portions, under an atmosphere of argon, to a solution of 73.9 g (0.3 mole) of ethyl 3-[(1H-imidazol-4-yl)methyl]-2-hydroxybenzoate (prepared in Example 7) in 4 liters of anhydrous tetrahydrofuran. The temperature increases progressively and, when the addition is complete, the mixture is heated under reflux for 3 hours. It is then cooled to 10° C. and 200 ml of ethyl acetate are added dropwise. The reaction mixture is evaporated under reduced pressure and the residue obtained is taken up in 1 liter of an ice-water mixture. The suspension is adjusted to pH 7.5 by the addition of concentrated hydrochloric acid. 700 ml of ethyl acetate are added thereto, followed by vigorous stirring for 30 minutes and then filtered. The filtrate is decanted and the aqueous phase is extracted 3 times with 500 ml of ethyl acetate. The organic phases are combined, dried over anhydrous magnesium sulfate, filtered and then evaporated under reduced pressure. There are obtained 61 g of an oil which crystallizes. The filter cake is carefully washed with ethyl acetate. The cake is taken up in 1.5 liter of ethyl acetate and extracted under reflux for 3 hours. It is then filtered and, after evaporation of the solvent under reduced pressure, 7 g of oil are recovered. The product is purified by chromatography on silica (eluent: 91.5:8:0.5 v/v/v dichloromethane-ethanolammonia) followed by recrystallization from ethyl acetate. There are obtained 33.8 g of 3-[(1H-imidazol-4-yl)methyl]-2-hydroxybenzenemethanol, which is identical with the compound obtained in Example 6.1. Yield: 55% of theory.

We claim:
1. A substituted 1H-imidazole, including its optically active isomers and racemic mixtures, of the formula

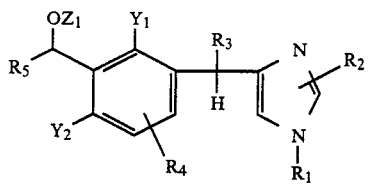 (I)

wherein
R$_1$, R$_2$, R$_3$ and R$_5$ each, independently, represent a hydrogen atom or an alkyl radical having 1 to 4 carbon atoms,
R$_4$ is a hydrogen atom, an alkyl radical having 1 to 4 carbon atoms or an alkoxy radical having 1 to 4 carbon atoms,
one of the symbols, Y$_1$ and Y$_2$ represents a hydrogen atom and the other an OZ$_2$ radical, and
Z$_1$ and Z$_2$ taken separately represent both a hydrogen atom or an alkyl radical having 1 to 4 carbon atoms and Z$_1$ and Z$_2$ taken together represent a —C$_2$— or —C(CH$_3$)$_2$— radical,
or a non-toxic pharmaceutically acceptable acid addition salt thereof.

2. A compound as claimed in claim 1, wherein
R$_1$, R$_2$, R$_4$ and R$_5$ each represent a hydrogen atom,
R$_3$ represents a hydrogen atom or an alkyl radical having 1 to 4 carbon atoms, and
Z$_1$ and Z$_2$ taken separately each represent a hydrogen atom and Z$_1$ and Z$_2$ taken together represent a —CH$_2$— or —C(CH$_3$)$_2$— radical,
or a non-toxic pharmaceutically acceptable acid addition salt thereof.

3. A compound as claimed in claim 1, namely 3-[(1H-imidazol-4-yl)methyl]-2-hydroxybenzenemethanol or a non-toxic pharmaceutically acceptable acid addition salt thereof.

4. A compound as claimed in claim 1, namely 3-[(1H-imidazol-4-yl)methyl]-6-hydroxybenzenemethanol or a non-toxic pharmaceutically acceptable acid addition salt thereof.

5. A compound as claimed in claim 1, namely 3-[1-(1H-imidazol-4-yl)ethyl]-2-hydroxybenzenemethanol or a non-toxic pharmaceutically acceptable acid addition salt thereof.

6. A compound as claimed in claim 1, namely 3-[(1-(1H-imidazol-4-yl)pentyl]-2-hydroxybenzenemethanol or a non-toxic pharmaceutically acceptable acid addition salt thereof.

7. A compound as claimed in claim 1, namely 4-[(4H-1,3-benzodioxin-8-yl)methyl]-1H-imidazole or a non-toxic pharmaceutically acceptable acid addition salt thereof.

8. A compound as claimed in claim 1, namely 4-[1-(4H-1,3-benzodioxin-8-yl)ethyl]-1H-imidazole or a non-toxic pharmaceutically acceptable acid addition salt thereof.

9. A compound as claimed in claim 1, namely 4-[(2,2-dimethyl-4H-1,3-benzodioxin-8-yl)methyl]-1H-imidazole or a non-toxic pharmaceutically acceptable acid addition salt thereof.

10. A compound as claimed in claim 1, namely 4-[1-(2,2-dimethyl-4H-1,3-benzodioxin-8-yl)ethyl]-1H-imidazole or a non-toxic pharmaceutically acceptable acid addition salt thereof.

11. A compound as claimed in claim 1, namely 4-[1-(2,2-dimethyl-4H-1,3-benzodioxin-8-yl)pentyl]-1H-imidazole or a non-toxic pharmaceutically acceptable acid addition salt thereof.

12. A process for the preparation of a substituted 1H-imidazole having the formula I given in claim 1, in which Z$_1$ and Z$_2$ taken separately represent an alkyl radical having 1 to 4 carbon atoms and taken together represent a —CH$_2$— or —C(CH$_3$)$_2$— radical, which comprises reducing an imidazole compound of the formula

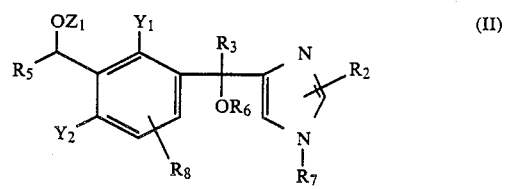 (II)

wherein R$_2$, R$_3$ and R$_5$ have the meanings given in claim 1, R$_6$ is a hydrogen atom or an alkyl radical having 1 to 4 carbon atoms, R$_7$ has the meaning as R$_1$ given in claim 1 or is a radical which can easily be removed by reduction, R$_8$ has the meaning as R$_4$ given in claim 1 or is a chlorine atom, one of the symbols Y$_1$ and Y$_2$ represents a hydrogen atom and the other an OZ$_2$ radical, and Z$_1$ and Z$_2$ have the meanings given above.

13. A process for the preparation of a substituted 1H-imidazole having the formula I given in claim 1, in which Z$_1$ and Z$_2$ are hydrogen atoms, which comprises hydrolyzing in an aqueous acid medium a 4-[[2,2-dimethyl-4H-1,3-benzodioxin-6(or 8)-yl]methyl]-1H-imidazole of the formula

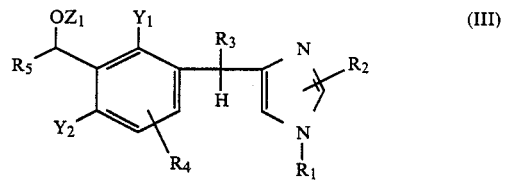 (III)

wherein R$_1$, R$_2$, R$_3$, R$_4$ and R$_5$ have the meanings given in claim 1, one of the symbols Y$_1$ and Y$_2$ represents a hydrogen atom and the other an OZ$_2$ radical, and Z$_1$ and Z$_2$ together represent the —C(CH$_3$)$_2$— radical.

14. A process for the preparation of a substituted 1H-imidazole having the formula I given in claim 1, in which Y$_1$=OZ$_2$ and Y$_2$, Z$_2$ and R$_5$ are hydrogen atoms, which comprises reducing an alkyl 3-[(1H-imidazol-4-yl)methyl]-2-hydroxybenzoate of the formula

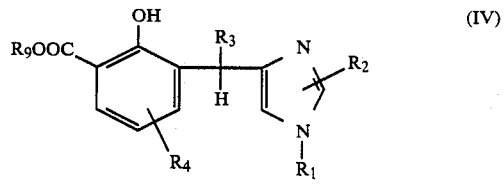 (IV)

wherein R$_1$, R$_2$, R$_3$ and R$_4$ have the meanings given in claim 1 and R$_9$ is an alkyl radical having 1 to 4 carbon atoms.

15. A pharmaceutical composition comprising a therapeutically effective amount of a substituted 1H-imidazole as claimed in claim 1 and a pharmaceutically acceptable solid or liquid diluent or carrier therefor.

16. A method for achieving an anti-ischemic effect in a patient in need thereof, which comprises administering to said patient an effective amount of a substituted 1H-imidazole as claimed in claim 1.

* * * * *